(12) United States Patent
Deng

(10) Patent No.: US 8,003,139 B2
(45) Date of Patent: Aug. 23, 2011

(54) PHARMACEUTICAL COMPOSITION FOR TREATING RHEUMATISM, AND METHOD OF MAKING SAME

(75) Inventor: Wenlong Deng, Chengdu (CN)

(73) Assignees: Sichuan Institute of Chinese Materia Medica, Chengdu, Sichuan (CN); Guangzhou Chen Li Ji Pharmaceutical Factory, Guangzhou, Guangdong (CN)

( * ) Notice: Subject to any disclaimer, the term of this patent is extended or adjusted under 35 U.S.C. 154(b) by 0 days.

(21) Appl. No.: 12/657,934

(22) Filed: Jan. 29, 2010

(65) Prior Publication Data
US 2010/0189825 A1 Jul. 29, 2010

Related U.S. Application Data

(63) Continuation-in-part of application No. 10/510,617, filed as application No. PCT/CN02/00246 on Apr. 9, 2002, now abandoned.

(51) Int. Cl.
*A61K 36/00* (2006.01)

(52) U.S. Cl. ........................................ 424/725

(58) Field of Classification Search ................ None
See application file for complete search history.

(56) References Cited

U.S. PATENT DOCUMENTS 6,280,751 B1 * 8/2001 Fletcher et al. ............... 424/401

FOREIGN PATENT DOCUMENTS

| CN | 1178697 |   | 4/1988 |
|----|---------|---|--------|
| CN | 1178697 | A | 4/1988 |
| CN | 1051859 | A | 6/1991 |
| CN | 1080177 | A * | 1/1994 |
| CN | 1097313 | A | 1/1995 |
| CN | 1142970 |   | 2/1997 |
| CN | 1146348 | A | 4/1997 |

OTHER PUBLICATIONS

International Search Report of PCT/CN2002/00246, dated Jan. 2, 2003.
Zhang Chun, Tripterygium bypoglaucum Hutch treating rheumatoid arthritis'; Hunan Journal of Traditional Chinese Medicine, 1988, vol. 4, No. 4, pp. 15 and 16 (and English Translation).
Chinese International Preliminary Examination Report, dated Aug. 19, 2004, for International Application No. PCT/CN02/00246; International Filing Date of Apr. 9, 2002.
English translation of International Preliminary Examination Report, dated Aug. 14, 2003, for International Application No. PCT/CN02/00246, International filing date of Apr. 9, 2002, in the name of Sichuan Institute of Chinese Materia Medica et al.
(U1) Green, J. The Herbal Medicine-Maker's Handbook: A Home Manual. 2000, Berkeley, California: The Crossing Press. pp. 108, 109, 112-114, 146-152, 154, 158-166, 292-304 and 309-311, particularly pp. 109, 112-114, 146, 151, 299, 309 and 310.
(V1) Hu, Y.; Zhang, R.; Tang, Q. and Wu, P. Se Pu. 1999; 17(3): 265-267. Abstract only.
(W1) Li, Z.; Liu, S.; Qian, G. and Li, P. Hua Xi Yi Ke Da Xue Xue Bao. 1995; 26(1): 66-69. Abstract only.
(X1) Xie, H. and Zhang, S. Se Pu. 1997; 15(1): 54-56. Abstract only.
(U2) Zhang, L.; Jiang, Z.; Tanaka, T. and Kouno, I. ZhongXu Zhong Yao Za Zhi. 1998; 23(9): 549-550. Abstract only.
Hanson, J. Diterpenoids; Nat. Prod. Rep. 1999, 16, 209-219.
Phillipson, J. New Drugs From Nature—it Could be Yew; Phytotherapy Research 13 (1999) pp. 2-8.
Revilla et al. Comparison of Several Procedures Used for the Extraction of Anthocynains From red Grapes; J. Agric. Food Chem. 1998, 46, pp. 4592-4597.

\* cited by examiner

*Primary Examiner* — Patricia Leith
(74) *Attorney, Agent, or Firm* — Christie, Parker & Hale, LLP

(57) ABSTRACT

A pharmaceutical composition for the treatment of rheumatism and a method of preparing it are provided. The composition consists of an alcoholic extract of 1-4 parts by weight *Tripterygium hypoglaucum* (Levl.) Hutch.; 1-4 parts by weight *Epimedium brevicornum* Maxim.; 1-4 parts by weight *Lycium barbarum* L.; and 1-4 parts by weight *Cuscuta chinensis* Lam., or *Cuscuta australis* R. Br. The composition has substantial therapeutic efficacy, with mild side effects, and is easy to administer.

3 Claims, No Drawings

PHARMACEUTICAL COMPOSITION FOR TREATING RHEUMATISM, AND METHOD OF MAKING SAME

CROSS-REFERENCE TO RELATED APPLICATIONS

This application is a continuation-in-part of U.S. application Ser. No. 10/510,617, filed Apr. 25, 2005, now abandoned which is a U.S. national stage application and claims the priority of International Application No. PCT/CN2002/00246, filed Apr. 9, 2002, the entire contents of both applications being incorporated by reference as if set forth in their entirety.

FIELD OF THE INVENTION

The present invention involves a medication and its method of preparation; in particular it involves a traditional anti-rheumatism Chinese medication and its method of preparation.

BACKGROUND OF THE INVENTION

Rheumatism and rheumatoid arthritis (RA) are generally considered to be difficult-to-treat diseases. Approximately 18 million RA patients are disabled by the disease. Research into new medications to treat RA has already been underway for almost a century. Aspirin was the earliest medication widely used for RA. Medications to treat RA may be generally divided into two types: non-steroidal anti-inflammatory drugs (NSAIDs) and immunosuppressants. NSAIDs include diclofenac and other anti-inflammatories and adrenal cortical hormones. Clinical studies demonstrate that NSAIDs are effective. Immunosuppressants and cytotoxic medications include methotrexate, cyclophosphamide, and penicillamine, among others. In recent years, immunomodulation has been used as a method for treating rheumatic diseases. All anti-rheumatism drugs have been shown to have serious side effects and to date, a high-efficacy, low-toxicity medication has not yet been developed.

There are three main areas of emphasis in the research and development of anti-rheumatism drugs. The first includes NSAIDs and cytokine antagonists, such as recombinant soluble tumor necrosis factor antagonists, interleukin-1 receptor antagonists and platelet activation factor inhibitors. The second area is new immunosuppressants or immunomodulators, such as cyclosporin A. The third area is compound medications.

Early treatment of bi syndrome (obstruction of qi and blood, RA) in the field of traditional Chinese medicine can be dated to the ancient Chinese physician Zhang Zhongjing, "decoction of herba ephedrae, semen armeniacae amarum, gypsum fibrosum and radix glycyrrhizae," "decoction of radix stephaniae tetrandrae and radix astragali" and "decoction of radix aconite." *Kniphofia uvaria* is a plant that grows wild in Sichuan Province, and in local area clinical trials (in Sichuan) it has been proven to have definite therapeutic efficacy for patients with rheumatism. Unfortunately, at the same time many uncontrollable problems and serious side effects on the human reproduction system have been observed.

In traditional Chinese medicine, there is a long history of treating bi syndrome, and in past eras, physicians have developed traditional Chinese medications to treat it. There are a number of medications with high therapeutic efficacy. In the 1995 and 2000 editions of the *Chinese Pharmacopeia* are collected no fewer than 80 single medications and 29 proprietary medications to treat bi syndrome. But there are problems, chiefly ① therapeutic efficacy against severe bi syndrome such as rheumatoid arthritis is still less than ideal, ② the preparation's dosage form cannot meet the needs of today's lifestyle, ③ a small number of medications possess therapeutic efficacy that could be termed good yet with major toxic side effects, such as the *Radix tripterygii wilfordii* preparation. This necessitates research and development of an anti-rheumatism medication with high efficacy and low toxicity, in a dosage form suited to today's lifestyle and medication-use habits, in particular a medication with treatment efficacy that can approach the efficacy of synthetic anti-rheumatism medications and has relatively mild side effects.

SUMMARY OF THE INVENTION

The objective of the present invention is to provide a compound medication with anti-rheumatism effect, high efficacy and low toxicity, and convenient administration. A further objective of the present invention is to provide a method for preparing the medication with anti-rheumatism effect.

The technical proposal for the medication of the present invention optimally is realized through the following materials:

*Tripterygium hypoglaucum* (Level) Hutch;
*Epimedium brevicornum* Maximowicz;
*Lycium barbarum* L.; and
*Cuscuta chinensis* Lamarck (or *Cuscuta australis* R. Br.).

DETAILED DESCRIPTION

The medication of the present invention is prepared from the above materials.

The materials may be composed of *Tripterygium hypoglaucum* (Level) Hutch together with any one or two or three of the other medications above.

The optimal materials formula proportions for the present invention are:

1-4 parts *Tripterygium hypoglaucum* (Level) Hutch by weight
1-4 parts *Epimedium brevicornum* Maximowicz by weight
1-4 parts *Lycium barbarum* L. by weight
1-4 parts *Cuscuta chinensis* Lamarck by weight Further, the optimal materials formula proportions for the present invention are:

2 parts *Tripterygium hypoglaucum* (Level) Hutch by weight
2 parts *Epimedium brevicornum* Maximowicz by weight
1 parts *Lycium barbarum* L. by weight
1 parts *Cuscuta chinensis* Lamarck by weight Further, the preferred materials formula proportions for the present invention are:

1-4 parts *Tripterygium hypoglaucum* (Level) Hutch by weight
1-4 parts *Epimedium brevicornum* Maximowicz by weight Further, the preferred materials formula proportions for the present invention are:

2 parts *Tripterygium hypoglaucum* (Level) Hutch by weight
2 parts *Epimedium brevicornum* Maximowicz by weight Further, the preferred materials formula proportions for the present invention are:

1-4 parts *Tripterygium hypoglaucum* (Level) Hutch by weight
1-4 parts *Epimedium brevicornum* Maximowicz by weight
1-4 parts *Lycium barbarum* L. by weight Further, the preferred materials formula proportions for the present invention are:

2 parts *Tripterygium hypoglaucum* (Level) Hutch by weight 2 parts *Epimedium brevicornum* Maximowicz by weight 1 part *Lycium barbarum* L. by weight Further, the preferred materials formula proportions for the present invention are:

1-4 parts *Tripterygium hypoglaucum* (Level) Hutch by weight 1-4 parts *Epimedium brevicornum* Maximowicz by weight 1-4 parts *Cuscuta chinensis* Lamarck by weight Further, the preferred materials formula proportions for the present invention are:

2 parts *Tripterygium hypoglaucum* (Level) Hutch by weight 2 parts *Epimedium brevicornum* Maximowicz by weight 1 part *Cuscuta chinensis* Lamarck by weight The amount of the glucoside $C_{33}H_{40}O_{15}$ from *Epimedium brevicornum* Maximowicz in the materials compound above should be no less than 2.0 mg.

Further, the preferred materials formula proportions for the present invention are:

1-4 parts *Tripterygium hypoglaucum* (Level) Hutch by weight and 1-4 parts *Lycium barbarum* L. by weight and/or 1-4 parts *Cuscuta chinensis* Lamarck by weight Further, the preferred materials formula proportions for the present invention are:

2 parts *Tripterygium hypoglaucum* (Level) Hutch by weight and 1 part *Lycium barbarum* L. by weight and/or 1 part *Cuscuta chinensis* Lamarck by weight With the above materials proportions by weight, routine preparation technology may be used to prepare any clinically acceptable medication form, such as pill, dispersant, cream, tablet, capsule (hard capsule or soft capsule), granule, injection, etc.

The method for preparing the medication of the present invention is:

Materials by Weight:

1-4 parts *Tripterygium hypoglaucum* (Level) Hutch by weight 1-4 parts *Epimedium brevicornum* Maximowicz by weight 1-4 parts *Lycium barbarum* L. by weight 1-4 parts *Cuscuta chinensis* Lamarck by weight After *Tripterygium hypoglaucum* (Level) Hutch and *Epimedium brevicornum* Maximowicz are each cut into pieces, water is added for 2-4 boilings. *Lycium barbarum* L. and *Cuscuta chinensis* Lamarck are each immersed in warm water at 80°-95° C. 1-3 times, and after the traditional Chinese medication decoction fluids and warm immersion fluids are blended, the blended mixture is placed in a corresponding large-pore adsorption resin column. When adsorption is complete, water is used to rinse the resin column until the liquid runs clear, followed by elution with 60-80% ethanol. When the runoff becomes darker in color, collection of the eluent is begun, until the color of the eluent turns from dark to extremely light. Water under pressure is used to expel the ethanol from the column, which is then blended with the eluent, the total eluent being approximately 3-8 times the amount of materials by weight. The eluent for each traditional Chinese medication respectively is recovered, concentrated to a 1.10 proportion, and respectively spray-dried to obtain the extract of the various materials. The four extracts are mixed thoroughly and prepared into any clinically acceptable dosage form.

The preferred technical steps for the method of the present invention are below:

2 parts *Tripterygium hypoglaucum* (Level) Hutch by weight 2 parts *Epimedium brevicornum* Maximowicz by weight 1 part *Lycium barbarum* L. by weight 1 part *Cuscuta chinensis* Lamarck by weight After *Tripterygium hypoglaucum* (Level) Hutch is cut into pieces, 13×, 10× and 10× the amount of water is added for three extractions, 1 h each time. After *Epimedium brevicornum* Maximowicz is cut into sections, 15×, 10× and 10× the amount of water is added for three extractions, 1 h each time. *Lycium barbarum* L. is pulverized to form a crude material, immersed in 20× water at 80° C. for 1 h, 3 times in succession. *Cuscuta chinensis* Lamarck is pulverized into a crude powder, immersed in 31× water at 80° C. for 1 h, in succession 3 times. The water decoctions or the water immersion liquids of the four materials are filtered separately and passed through a large-pore adsorption resin column JD-1 (WLD). 70% ethanol is used for elution. When the color of the runoff liquid is clearly darker, collection of eluent is started. When the eluent color becomes extremely light the elution is complete. Ethanol is recovered from each eluent of the materials, which is concentrated and dried to finally obtain the extracted materials powders. Each of the four extracted powders of materials is mixed thoroughly and prepared into any clinically acceptable dosage form.

The preparation of the materials in the present invention may further employ the following methods.

The raw materials are weighed, and the *Epimedium brevicornum* Maximowicz and the *Tripterygium hypoglaucum* (Level) Hutch are cut into pieces. The *Lycium barbarum* L. and the *Cuscuta chinensis* Lamarck are in raw form or pulverized, the four ingredients above are each or in combination extracted using 0-95% ethanol at 10-98° C., in succession 1-4 times. After ethanol is recovered from the extraction fluid separately or in combination, the fluid is concentrated, dried, pulverized, mixed thoroughly or mixed in proportion, to prepare a clinically acceptable dosage form.

Further, the materials of the present invention are formed into active ingredients using the raw materials above.

Of the above-described raw materials, *Epimedium brevicornum* Maximowicz contains icariine, icariside I, icariside II and icariine A, *Tripterygium hypoglaucum* (Level) Hutch contains diterpenes, triterpenes and biological alkaloid compounds. The chief components in *Cuscuta chinensis* Lamarck and *Lycium barbarum* L. are flavones.

Thus, preparation of *Epimedium brevicornum* Maximowicz in the present invention can be replaced with one or more of icariine, icariside I, icariside II and icariine A. *Tripterygium hypoglaucum* (Level) Hutch can be replaced by the diterpenes, triterperies and biological alkaloid compounds contained in *Tripterygium hypoglaucum* (Level) Hutch, and *Cuscuta chinensis* Lamarck and *Lycium barbarum* L. can be replaced by their flavone components.

The medication of the present invention (Fengshiping capsules) has undergone pharmacodynamic study and it has been proven that when Fengshiping is administered by perfusion, it is able to clearly inhibit primary and secondary damage in the rat adjuvant arthritis (AA) model; to clearly inhibit 2,4-dinitrofluorobenzene (DNFB)-induced delayed type hypersensitivity (DTH) in the ear of the mouse; to clearly inhibit hemolysin antibody formation in macrophages in the mouse, spleen cell IL-1, IL-2, IL-6 and TNF activity. Fengshiping is able to clearly inhibit ConA-induced lymphocyte transformation, Fengshiping is able to clearly inhibit $CD_4$ and $CD_8$ cells, although its effect on $CD_4$ is stronger, it had no clear effect on the $CD_4/CD_8$ ratio. The above-described Fengshiping effects all have a clear, linear dosage-efficacy relationship. 12-18 g/kg (crude drug) is the minimum effective dose. Fengshiping also clearly inhibits NK cells. However, Fengshiping at effective doses does not cause atrophy of the thymus gland, the spleen and other immunity organs and it also does not inhibit the phagocytic effect of macrophages.

Fengshiping clearly inhibits the inflammation response. It is able to inhibit acetic acid-induced abdominal cavity capillary vessel hyperpermeability in mice; to express croton oil-induced ear inflammation; and carrageenan-induced pleuritis in mice and white blood cell aggregation in CMC sacs in rats. However, Fengshiping is weaker in inhibiting carrageenan-induced foot inflammation and granuloma tissue proliferation. In addition to this, Fengshiping clearly inhibits the acetic acid-induced body-twisting response in mice.

Experiment 1: Effect on Adjuvant Arthritis (AA)

1.1 Preventive Effect Against Rat AA.

72 SD isogenous rats, littermates, half male and half female, weighing 180-220 g, were randomly divided into 6 groups, 12 animals per group, in separate cages, 6 animals per cage. Precise narrowband tape measures were used to obtain the rats' left and right rear ankle joint and foot maximum circumference to serve as the normal value. All were administered by perfusion administration the same volume of different doses of medication or the same volume of an *Astragalus* solution. 1 h after administration, through the left rear foot pad, each group of rats was injected intradermally with 0.1 mL Freund's complete adjuvant per animal. The medication was perfused once a day, for 30 days. The same method was used to obtain the rats' left and right ankle joint and foot circumference. A preventive medication administration test was used to detect daily mouse foot circumference minus the pre-inflammation circumference of the mouse foot to calculate the level of inflammation (Δ cm). The results are shown in Tables 1.1 and 1.2. At the end date, body weight and weight of the main organs were obtained. The results are shown in Tables 1.3 and 1.4.

TABLE 1.1

Effect of Fengshiping on AA mice foot-ankle joint inflammation.

| Group | Dose (g/kg) | Level of inflammation (□ cm) | | | | | | |
|---|---|---|---|---|---|---|---|---|
| | | 1 d | 2 d | 3 d | 9 d | 12 d | 14 d | 16 d |
| Control | — | 0.69 ± 0.17 | 0.69 ± 0.12 | 0.92 ± 0.18 | 0.84 ± 0.41 | 1.10 ± 0.30 | 1.65 ± 0.68 | 2.10 ± 0.55 |
| Fengshiping | 7.5 | 0.74 ± 0.12 | 0.66 ± 0.074 | 0.83 ± 0.13 | 0.77 ± 0.27 | 1.11 ± 0.45 | 1.34 ± 0.53 | 1.91 ± 0.61 |
| Fengshiping | 15 | 0.80 ± 0.24 | 0.62 ± 0.13 | 0.76 ± 0.18 | 0.49 ± 0.17* | 0.73 ± 0.34* | 1.00 ± 0.48* | 1.38 ± 0.67* |
| Fengshiping | 30 | 0.75 ± 0.19 | 0.67 ± 0.19 | 0.87 ± 0.28 | 0.63 ± 0.22 | 0.73 ± 0.34* | 0.82 ± 0.43** | 1.05 ± 0.53** |
| *Tripterygium hypoglaucum* (Level) Hutch | 5 | 0.72 ± 0.11 | 0.68 ± 0.16 | 0.91 ± 0.18 | 0.66 ± 0.23 | 0.88 ± 0.29 | 1.03 ± 0.36* | 1.37 ± 0.33* |
| Prednisone | 0.01 | 0.64 ± 0.14 | 0.64 ± 0.16 | 0.50 ± 0.26 | 0.46 ± 0.25 | 0.72 ± 0.46* | 0.87 ± 0.46** | 1.28 ± 0.69* |

| Group | Dose (g/kg) | Level of inflammation (□ cm) | | | | | |
|---|---|---|---|---|---|---|---|
| | | 18 d | 20 d | 22 d | 24 d | 26 d | 28 d |
| Control | — | 2.18 ± 0.44 | 2.05 ± 0.46 | 2.0 ± 0.46 | 2.04 ± 0.57 | 1.92 ± 0.65 | 1.83 ± 0.67 |
| Fengshiping | 7.5 | 1.74 ± 0.73 | 1.81 ± 0.55 | 1.81 ± 0.52 | 1.77 ± 0.55 | 1.65 ± 0.55 | 1.55 ± 0.49 |
| Fengshiping | 15 | 1.32 ± 0.59** | 1.28 ± 0.58** | 1.34 ± 0.61* | 1.33 ± 0.67* | 1.20 ± 0.64* | 1.08 ± 0.58** |
| Fengshiping | 30 | 0.95 ± 0.50** | 0.87 ± 0.51** | 0.95 ± 0.54** | 0.89 ± 0.59** | 0.90 ± 0.57** | 0.86 ± 0.51** |
| *Tripterygium hypoglaucum* (Level) Hutch | 5 | 1.47 ± 0.43** | 1.50 ± 0.43** | 1.49 ± 0.43* | 1.42 ± 0.53* | 1.40 ± 0.56* | 1.32 ± 0.57* |
| Prednisone | 0.01 | 1.18 ± 0.76 | 1.03 ± 0.67 | 1.05 ± 0.69* | 0.90 ± 0.64 | 0.86 ± 0.65 | 0.85 ± 0.59** |

Compared to control group *P < 0.05, ** P< 0.01 (same below)

TABLE 1.2

Effect of Fengshiping on AA mice on the foot-ankle joint inflammation.

| Group | Dose (g/kg) | Level of inflammation (□ cm) | | | | | |
|---|---|---|---|---|---|---|---|
| | | 2 d | 9 d | 12 d | 14 d | 16 d | 18 d |
| Control | — | 0.14 ± 0.05 | 0.06 ± 0.10 | 0.34 ± 0.36 | 0.80 ± 0.52 | 1.43 ± 0.67 | 1.36 ± 0.61 |
| Fengshiping | 7.5 | 0.18 ± 0.06 | 0.10 ± 0.014 | 0.26 ± 0.36 | 0.82 ± 0.52 | 1.31 ± 0.64 | 1.28 ± 0.71 |
| Fengshiping | 15 | 0.15 ± 0.08 | 0.02 ± 0.06 | 0.13 ± 0.10* | 0.37 ± 0.31* | 0.90 ± 0.56* | 0.79 ± 0.60* |
| Fengshiping | 30 | 0.18 ± 0.09 | 0.06 ± 0.06 | 0.16 ± 0.08* | 0.29 ± 0.20** | 0.49 ± 0.41* | 0.33 ± 0.29** |
| *Tripterygium hypoglaucum* (Level) Hutch | 5 | 0.16 ± 0.07 | 0.01 ± 0.07 | 0.11 ± 0.10 | 0.44 ± 0.19** | 0.87 ± 0.56* | 0.84 ± 0.67* |
| Prednisone | 0.01 | 0.20 ± 0.06 | 0.08 ± 0.08 | 0.21 ± 0.16 | 0.44 ± 0.43 | 0.99 ± 0.63 | 0.84 ± 0.74* |

| Group | Dose (g/kg) | Level of inflammation (□ cm) | | | | | |
|---|---|---|---|---|---|---|---|
| | | 20 d | 22 d | 24 d | 26 d | 28 d | |
| Control | — | 1.28 ± 0.57 | 1.38 ± 0.64 | 1.35 ± 0.75 | 1.20 ± 0.78 | 1.12 ± 0.63 | |
| Fengshiping | 7.5 | 1.33 ± 0.71 | 1.31 ± 0.73 | 1.27 ± 0.73 | 1.16 ± 0.73 | 1.07 ± 0.65 | |
| Fengshiping | 15 | 1.74 ± 0.57* | 1.92 ± 0.61* | 0.95 ± 0.64* | 0.88 ± 0.58* | 1.83 ± 0.55 | |
| Fengshiping | 30 | 0.27 ± 0.30** | 0.34 ± 0.31** | 0.32 ± 0.33** | 0.31 ± 0.32** | 0.34 ± 0.32** | |
| *Tripterygium hypoglaucum* (Level) Hutch | 5 | 0.82 ± 0.65* | 0.89 ± 0.70* | 0.80 ± 0.67* | 0.83 ± 0.68** | 0.75 ± 0.69 | |
| Prednisone | 0.01 | 0.82 ± 0.72** | 0.79 ± 0.74* | 0.75 ± 0.67** | 0.68 ± 0.64* | 0.71 ± 0.67 | |

TABLE 1.3

Effect of Fengshiping on AA mice in body weight.

| | | | Change in body weight (g) | |
|---|---|---|---|---|
| Group | Dose (g/kg) | Initial body weight | AA 1 month body weight | Increase in body weight |
| Control | — | 228 ± 34 | 231 ± 52 | 3 |
| | 7.5 | 229 ± 34 | 220 ± 46 | −9 |
| Fengshiping | 15 | 223 ± 40 | 232 ± 34 | 9 |
| | 30 | 224 ± 37 | 256 ± 60 | 32 |
| *Tripterygium hypoglaucum* (Level) Hutch | 5 | 226 ± 45 | 230 ± 43 | 4 |
| Prednisone | 0.01 | 264 ± 55 | 244 ± 31 | −21 |

TABLE 1.4

Effect of Fengshiping on AA mice organ weight (preventive).

| | Dose | Organ system (g tissue/100 g body weight) | | | |
|---|---|---|---|---|---|
| Group | (g/kg) | Liver | Spleen | Thymus gland | Adrenal gland |
| Control | — | 3.92 ± 0.65 | 0.34 ± 0.10 | 0.098 ± 0.40 | 0.027 ± 0.01 |
| Fengshiping | 7.5 | 3.73 ± 0.29 | 0.31 ± 0.09 | 0.078 ± 0.038 | 0.027 ± 0.008 |
| Fengshiping | 15 | 3.48 ± 0.32 | 0.38 ± 0.10 | 0.100 ± 0.034 | 0.023 ± 0.005 |
| Fengshiping | 30 | 3.38 ± 0.28* | 0.44 ± 0.12* | 0.100 ± 0.032 | 0.022 ± 0.007 |
| *Tripterygium hypoglaucum* (Level) Hutch | 5 | 3.21 ± 0.30** | 0.36 ± 0.05 | 0.052 ± 0.011** | 0.026 ± 0.009 |
| Prednisone | 0.01 | 3.04 ± 0.20** | 0.32 ± 0.08 | 0.050 ± 0.060** | 0.020 ± 0.004* |

1.2 Therapeutic Effect on AA Rats.

50 male SD rats were randomly divided into 5 groups and subjected to the same method. However 13 days after starting injection by perfusion with Freund's adjuvant to induce inflammation, once a day, for 2 weeks, the daily circumference measurement was subtracted from the circumference at the start of medication administration to calculate the level of inflammation (A cm). For results see Tables 1.5 and 1.6. For main organ weights see Table 1.7.

TABLE 1.5

Therapeutic effect of Fengshiping on AA rats and foot-ankle joint inflammation

| | Dose | Inflammation (□ cm) | | | |
|---|---|---|---|---|---|
| Group | (g/kg) | 1 d | 2 d | 4 d | 6 d |
| Control | — | 1.81 ± 0.27 | 1.92 ± 0.19 | 2.12 ± 0.22 | 2.16 ± 0.27 |
| Fengshiping | 7.5 | 1.68 ± 0.50 | 1.64 ± 0.54 | 1.70 ± 0.57 | 1.82 ± 0.61 |
| Fengshiping | 15 | 1.44 ± 0.41* | 1.51 ± 0.36** | 1.65 ± 0.34** | 1.74 ± 0.31** |
| Fengshiping | 30 | 1.50 ± 0.56 | 1.48 ± 0.41** | 1.51 ± 0.44** | 1.59 ± 0.51** |
| Prednisone | 0.01 | 1.78 ± 0.51 | 1.70 ± 0.51 | 1.63 ± 0.50* | 1.58 ± 0.50** |

| | Dose | Inflammation (□ cm) | | | |
|---|---|---|---|---|---|
| Group | (g/kg) | 8 d | 10 d | 12 d | 14 d |
| Control | — | 1.92 ± 0.32 | 1.87 ± 0.34 | 1.92 ± 0.39 | 1.78 ± 0.44 |
| Fengshiping | 7.5 | 1.67 ± 0.68 | 1.60 ± 0.71 | 1.61 ± 0.77 | 1.58 ± 0.71 |
| Fengshiping | 15 | 1.46 ± 0.37** | 1.48 ± 0.30* | 1.28 ± 0.37** | 1.22 ± 0.38** |
| Fengshiping | 30 | 1.29 ± 0.58** | 1.29 ± 0.65** | 1.26 ± 0.67** | 1.20 ± 0.68* |
| Prednisone | 0.01 | 1.27 ± 0.46** | 1.09 ± 0.54** | 0.94 ± 0.50** | 0.94 ± 0.42** |

TABLE 1.6

Therapeutic effect of Fengshiping on AA rats on opposite side ankle joint inflammation.

| Group | Dose (g/kg) | Inflammation (□ cm) | | | |
|---|---|---|---|---|---|
| | | 2 d | 4 d | 6 d | 8 d |
| Control | — | 0.36 ± 0.26 | 0.45 ± 0.25 | 0.55 ± 0.34 | 0.47 ± 0.29 |
| Fengshiping | 7.5 | 0.12 ± 0.25 | 0.34 ± 0.32 | 0.48 ± 0.41 | 0.28 ± 0.38 |
| Fengshiping | 15 | 0.21 ± 0.18 | 0.38 ± 0.27 | 0.44 ± 0.33 | 0.21 ± 0.33* |
| Fengshiping | 30 | 0.10 ± 0.48 | 0.06 ± 0.28** | 0.11 ± 0.24** | 0.06 ± 0.27** |
| Prednisone | 0.01 | 0.10 ± 0.13* | 0.15 ± 0.28* | 0.11 ± 0.25** | −0.08 ± 0.34** |

| Group | Dose (g/kg) | Inflammation (□ cm) | | |
|---|---|---|---|---|
| | | 10 d | 12 d | 14 d |
| Control | — | 0.48 ± 0.25 | 0.46 ± 0.31 | 0.40 ± 0.36 |
| Fengshiping | 7.5 | 0.35 ± 0.30 | 0.30 ± 0.29 | 0.30 ± 0.35 |
| Fengshiping | 15 | 0.19 ± 0.45* | 0.06 ± 0.31** | −0.06 ± 0.34** |
| Fengshiping | 30 | 0.02 ± 0.39** | 0.05 ± 0.38* | −0.02 ± 0.41** |
| Prednisone | 0.01 | −0.13 ± 0.28 | −0.26 ± 0.36 | −0.33 ± 0.39** | n = 10, compared to control group, *P < 0.05, **P < 0.01

1.7 Effect of Fengshiping on AA rat body weight and immune system organ weight.

| Group | Dose (g/kg) | Organ index (g tissue/100 g body weight) | | | |
|---|---|---|---|---|---|
| | | Liver | Spleen | Thymus gland | Adrenal gland |
| Control | — | 0.35 ± 0.23 | 0.35 ± 0.061 | 0.078 ± 0.014 | 0.026 ± 0.0071 |
| Fengshiping | 7.5 | 3.21 ± 0.52 | 0.33 ± 0.091 | 0.071 ± 0.026 | 0.024 ± 0.0085 |
| Fengshiping | 15 | 3.40 ± 0.54 | 0.36 ± 0.014 | 0.067 ± 0.022 | 0.023 ± 0.0048 |
| Fengshiping | 30 | 2.79 ± 0.43 | 0.32 ± 0.014 | 0.069 ± 0.029 | 0.023 ± 0.0072 |
| *Tripterygium hypoglaucum* (Level) Hutch | 5 | 3.92 ± 0.59 | 0.35 ± 0.083 | 0.075 ± 0.034 | 0.027 ± 0.0060 |
| Prednisone | 0.01 | 3.52 ± 0.35 | 0.28 ± 0.047* | 0.05 ± 0.011** | 0.02 ± 0.0043* |

From Tables 1.1, 1.2, 1.3, 1.5 and 1.6 it can be seen that Fengshiping had a strong inhibitory effect on primary damage from the adjuvant arthritis rat model at the injection side and secondary joint damage on the opposite side. At the time of induced inflammation and 2 weeks after induced inflammation, medication administration gave clear results, demonstrating that Fengshiping had a clear preventive and therapeutic effect on adjuvant arthritis in the rat. Comparison of the effect of Fengshiping on rat rear limb-ankle joint specific immunity inflammation and mouse foot non-specific inflammation shows that Fengshiping effect on ankle joint inflammation was strong, demonstrating the main effect of Fengshiping in inhibiting the immunity inflammation response.

The results in Tables 1.3, 1.4 and 1.7 demonstrate that, throughout the experimental period, the AA rats showed no clear increase in body weight, and when Fengshiping was at the effective dose, rat body weight increased. In the prednisone therapy and prevention group all rat body weights declined, and the thymus gland and the adrenal gland clearly atrophied. In *Tripterygium hypoglaucum* (Level) Hutch alone, thymus gland atrophy could also be seen, however, the three Fengshiping doses did not appear to have a clear effect on thymus gland and adrenal gland weight.

1.3. Pathological Changes in AA Rat Model After Treatment

45 SD rats were divided, into 6 groups, weight 180 20 g. After Freund's adjuvant was used to cause AA, Fengshiping by perfusion was administered for 5 days. 1 h after the final administration, evaluation was performed and the rat arthritis index was calculated. Secondary damage to the rat on the side of the rear limb joint was fixed using formaldehyde, and stained with HE, and changes to joint synovial membrane and cartilage were observed under microscope. Rat joint index results for each group are shown in Table 1.8.

TABLE 1.8

Fengshiping effect on AA rat joint index.

| Group | Dose (g/kg) | Number of rats (per group) | Joint index |
|---|---|---|---|
| Control group | — | 8 | 0** |
| AA model group | — | 7 | 6.2 ± 0.49 |
| Fengshiping | 7.5 | 9 | 4.86 ± 0.90** |
| Fengshiping | 15 | 7 | 4.71 ± 0.95** |
| Fengshiping | 30 | 7 | 4.56 ± 1.13** |
| *Tripterygium wilfordii* polyglucoside | 0.006 | 7 | 4.57 ± 0.79** |

Compared to model group
**P < 0.01

The joint index was scored based on redness and inflammation of each joint of the rat, from 0-4 points. The four limb scores were totaled to create the joint index. The four limbs and the joint scoring standards follow: 0 points=normal, 1 point=redness only, 2 points=redness and mild inflammation, 3 points=severe inflammation, 4 points=joint deformation and rigidity.

Under a microscope, it could be observed that the rats in the model group in which the rear limb joint synovial membrane had grown, collagen fibers had increased, lymphocytes and plasma cells had infiltrated, a clear granuloma formed. The synovial membrane cells degenerated, the cytoplasm stained red, the cell nucleus had undergone pycnosis, in some areas the synovial membrane epidermis had worn away, the cartilage atrophied, the surface being rough, bumpy and uneven, and there was a slight increase in cartilage cells. After treatment with the various Fengshiping dose groups, joint synovial membrane tissue inflammation was lessened and more collagen fibers formed. The synovial membrane cells were less worn away, cartilage surface cells increased, the surface was smoothened, and the cartilage was recovering.

In control group rats, proliferation of synovial membrane layers could be seen. There was increased collagen fiber and lymphocyte and plasma cell infiltration, the formation of a clear granuloma, synovial cell degeneration, red staining of the cytoplasm; cell nucleus pycnosis, and in some areas synovial epidermis was worn away. In the Fengshiping treatment group, joint synovial tissue inflammation was lessened, more collagen fibers formed, synovial membrane cells were less worn away, cartilage surface cells increased, the surface smoothened and the cartilage was in recovery.

Experiment 2. 50 NIH mice with 2,4-dinitrofluorobenzene (DNFB)-induced delayed type hypersensitivity (DTH) reaction in the ear, half male and half female, were randomly divided into 5 groups. A 0.025 mL 1% DNFB acetone solution was applied to sites with the abdominal hair removed to induce sensitivity. On alternate days, the same method was used to intensify one time, and on the fifth day after sensitivity was induced a 0.01 mL 1% DNFB food oil solution was smeared on the right ear of the animal, at 24 h the mouse was sacrificed. A balanced twisting force was used equally on the left and the right ears to determine the difference in weight (mg) between the two, which served as the mouse's DTH reaction intensity. The experiment was carried out on the different immunities and administration methods.

2.1 Effect of Full Course Administration on DTH

The immunity and medication administration procedures are below:

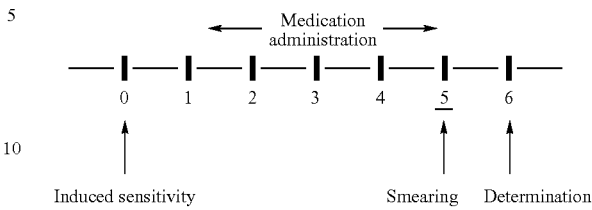

TABLE 2.1

Effect of Fengshiping on NIH mouse DNFB-induced delayed type hypersensitivity reaction.

| Group | Dose (g/kg) | Administration Time | Number of mice (per group) | Ear inflammation percentage | Inhibition rate | P value |
|---|---|---|---|---|---|---|
| Control | | | 10 | 34.20 ± 3.77 | | |
| Fengshiping | 27 | 0-5 | 10 | 26.24 ± 3.34 | 23.3 | <0.01 |
| Fengshiping | 40 | 0-5 | 10 | 12.99 ± 4.96 | 62.0 | <0.01 |
| Fengshiping | 60 | 0-5 | 10 | 10.43 ± 7.53 | 69.5 | <0.01 |
| Dexamethasone | 0.003 | 0-5 | 10 | 13.93 ± 4.41 | 59.3 | <0.01 |
| Control | | | 10 | 42.43 ± 5.28 | | |
| Fengshiping | 40 | −2-0 | 10 | 31.50 ± 10.52 | 25.0 | <0.01 |
| Fengshiping | 40 | −2-2 | 10 | 30.88 ± 7.92 | 27.2 | <0.01 |
| Fengshiping | 40 | −2-5 | 10 | 21.07 ± 4.62* | 50.3 | <0.01 |
| Fengshiping | 40 | −5-6 | 10 | 32.00 ± 9.37 | 41.7 | <0.01 |
| Cyclophosphamide | 0.05 | −2-2 | 10 | 39.40 ± 10.78 | 8.1 | <0.05 |
| Cyclophosphamide | 0.05 | −2-0 | 10 | 37.47 ± 6.71 | 11.7 | <0.05 |
| Control | | | 10 | 38.50 ± 4.67 | | |
| Cy | 0.1 *3 | Once, days 0, 2, 4 | 10 | 23.00 ± 7.65 | 40.3 | <0.01 |
| Cy | 0.25 | −3 d | 10 | 41.84 ± 7.75 | −8.7 | |
| Fengshiping | 60 | 0-4 | 10 | 27.20 ± 10.20 | 29.4 | <0.01 |
| Cy + Fengshiping | 0.25 + 60 | −3, 0-4 | 10 | 38.07 ± 6.65 | 1.1 | |

*Compared to the various other groups P < 0.05 or P < 0.01

From the results in Table 2.1 it can be seen that Fengshiping has a clear inhibitory effect on DNFB-induced murine DTH, and the intensity of its inhibitory effect has a clear dose relationship. A larger dose gives a stronger effect, at 60.9 g/kg it can cause the DTH inhibition rate to reach 69.5%.

2.2 Effect of Different Medication Administration Times on Murine DTH.

Immunity and medication administration procedures and results can be seen in the center columns and lower columns of Table 2.1. The table's center columns show 2 days before and the day sensitivity was induced, 2 days before sensitivity was induced to 2 days after sensitivity was induced, 2 days before sensitivity was induced to 5 days after sensitivity was induced, and medication administered before and after the smearing. In all cases the murine DTH reaction was inhibited, however the inhibitory effect was especially strong prior to inducing sensitivity and after inducing sensitivity; the entire medication administration procedure—that is, administration 2 days before inducing sensitivity to 5 days after inducing sensitivity, indicates that Fengshiping inhibition of the DTH effect and the mechanism may also be related to inhibition of the DTH reaction's early-stage participation in the cells and related to inhibition of DTH late-stage effective cells and DTH reaction mid-stage cells, different from cyclophosphamide. When cyclophosphamide was administered 2 days prior to induced sensitivity until the day sensitivity was induced or 2 days after induced sensitivity, smaller doses did not affect the DTH reaction.

From the lower columns of Table 2.1 it can be seen that when a single large dose of cyclophosphamide was administered three days before sensitivity was induced, intense inhibition of Ts cells made Th cells relatively hyperfunctional, which showed that not only did it not inhibit the murine DTH reaction, on the contrary, there was increased strength. At this point if it were to be used with Fengshiping, which has clear DTH inhibition results, the inhibition efficacy of Fengshiping would be cancelled out, which shows that the mechanism of effect of Fengshiping inhibition of the DTH reaction differs from that of cyclophosphamide and may be relatively sensitive to the inhibitory effect against TH cells.

Experiment 3. Effect on Humoral Immunity 3.1 Effect on Chicken Red Blood Cell (CRBC) Immunity Induced in Normal Murine Hemolysin Antibody Formation 190 mice of 18-22 g, half male and half female, were randomly divided into 19 groups. Each group was immunized with 0.2 mL IP 5% CRBC. At 7 days after immunization, blood was taken from the eyeballs. After dilution with physiological saline, the effect of Fengshiping on murine hemolysin antibodies was determined for each group of mice. Fengshiping immunity perfusion started at different times. The results are shown in Tables 3.1, 3.2 and 3.3.

From the results in the three tables above it can be seen that Fengshiping creates a clear inhibitory effect on hemolysin antibodies in different strains of mice, and as the dose is increased the effect is strengthened; it has a good dose-efficacy relationship. The lowest inhibition dose is 12 g/kg, compared to the Fengshiping group formed from *Tripterygium hypoglaucum* (Level) Hutch as one of the chief components, the inhibitory effect created against the antibody is clearly strong. The results in Table 3.1 show that the intensity of Fengshiping's effect is about 2.25 times or higher (effect of 13.5 kg *Tripterygium hypoglaucum* (Level) Hutch is weak compared to the effect of Fengshiping containing 6 g/kg *Tripterygium hypoglaucum* (Level) Hutch).

3.2 Effect on AA Mouse Humoral Immune Function

The right rear foot metatarsal of NIH mice, weighing 20±2 g, was intradermally injected with 0.05 mL of Freund's complete adjuvant. After 3 weeks an AA mouse model was created, after they were randomly divided into 6 groups, each mouse was perfused with different medications for 5 days. At the start of administering medication at the same time, 0.5 mL IP 10% sheep red blood cells (SRBC) was administered to

TABLE 3.1

Effect of Fengshiping on NIH murine hemolysin antibody formation

| Group | Dose (g/kg) | Medication administration time | Number of mice (per group) | Hemolysin value | Inhibition rate | P value |
|---|---|---|---|---|---|---|
| Control | | | 10 | 169.0 ± 62.0 | | |
| Fengshiping | 18 | 0-7 | 10 | 46.0 ± 15.6 | 72.8 | <0.01 |
| Fengshiping | 27 | 0-7 | 10 | 35.4 ± 12.0 | 79.1 | <0.01 |
| Fengshiping | 40 | 0-7 | 10 | 28.2 ± 5.9 | 83.3 | <0.01 |
| Fengshiping | 60 | 0-7 | 10 | 16.7 ± 3.0 | 90.1 | <0.01 |
| *Tripterygium hypoglaucum* (Level) Hutch | 13.3 | 0-7 | 10 | 121.0 ± 88.0** | 28.4 | <0.015 |
| Cyclophosphamide | 0.02 | 0-7 | 10 | 35.0 ± 12.0 | 79.3 | <0.01 |

**Compared to Fengshiping containing identical *Tripterygium hypoglaucum* (Level) Hutch (40 g/kg) P < 0.01

TABLE 3.2

Effect of Fengshiping on ICR murine hemolysin antibody formation

| Group | Dose (g/kg) | Medication administration time | Number of mice (per group) | Hemolysin value | Inhibition rate | P value |
|---|---|---|---|---|---|---|
| Control | — | — | 10 | 124.70 ± 2.60 | | |
| Fengshiping | 12 | 0-7 | 10 | 75.00 ± 53.10 | 39.9 | <0.05 |
| Fengshiping | 18 | 0-7 | 10 | 45.60 ± 22.70 | 63.4 | <0.01 |
| Fengshiping | 27 | 0-7 | 10 | 29.10 ± 22.10 | 76.8 | <0.01 |
| Fengshiping | 40 | 0-7 | 10 | 28.20 ± 5.30 | 77.4 | <0.01 |
| *Tripterygium hypoglaucum* (Level) Hutch | 6.0 | 0-7 | 10 | 143.50 ± 67.90** | | >0.05 |
| Cyclophosphamide | 0.02 | 0-7 | 10 | 27.80 ± 6.60 | 77.9 | <0.01 |

Compared to Fengshiping identical dose (18 g/kg) P < 0.01

TABLE 3.3

Effect of Fengshiping on ICR murine hemolysin antibody formation

| Group | Dose (g/kg) | Medication administration time | Number of mice (per group) | Hemolysin value | Inhibition rate | P value |
|---|---|---|---|---|---|---|
| Control | — | — | 10 | 256.0 ± 26.0 | | |
| Fengshiping | 18 | −7-7 | 10 | 198.0 ± 50.0 | 22.7 | <0.01 |
| Fengshiping | 18 | −3-7 | 10 | 156.0 ± 85.0 | 39.1 | <0.01 |
| Fengshiping | 18 | 0-7 | 10 | 98.0 ± 35.0 | 61.7 | <0.01 |
| Cyclophosphamide | 0.02 | 0-7 | 10 | 25.0 ± 4.0 | 90.2 | <0.01 | induce sensitivity. After 5 days the mice were sacrificed, the spleens obtained and after rinsing in Hank's solution, a lymphocyte suspension was prepared. The cell concentration was adjusted to $2\times10^7$/mL, 1 mL added to test tubes, 1 mL 0.2% SRBC and 1 mL 1:30 complement added, followed by incubation in a 37° C. water bath for 1 h and centrifugation at 2000 rpm for 5 min. the supernatant was obtained, and 722 spectrophotometry was used to count at a wavelength at 415 nm to detect the optical density and represent the PFC count.

Blood was obtained from the sensitivity-induced mice, the serum was separated, and an agglutination test used to determine the antibody efficacy value, expressed using a Log 2 value. The results are shown in Table 3.4.

scribed egg albumin serum (diluted 1:5 and 1:10, each labeled $d_1$, $d_2$); each dilution degree was 2 points. After 48 h, 1 mg 0.5% Evans blue physiological saline solution containing egg albumin in 1 mL IV was administered. After 20 min the rat was sacrificed by decapitation and its dorsal skin was turned back. Based on the nucleus ceruleus color intensity and area, dye exudation intensity was used to evaluate the nucleus ceruleus grade, then the blue-dyed skin was cut into pieces, immersed in 5 M 10.1% acetone sulfate (7:3) solution, centrifuged after 48 h, and the supernatant optical density was measured at 590 nm to calculate the PCA reaction strength and inhibition percentage for the various rat groups. The results are shown in Table 4.

TABLE 4

Effect of Fengshiping on rat PCA

| Group | Dose (g/kg) | Subvalue | | Absorbance | |
|---|---|---|---|---|---|
| | | Liver | Spleen | Thymus gland | Adrenal gland |
| Control | — | 5.60 ± 1.78 | 2.40 ± 2.46 | 0.191 ± 0.129 | 0.096 ± 0.106 |
| Fengshiping | 12 | 7.50 ± 2.51 | 4.20 ± 2.49 | 0.402 ± 0.213* | 0.192 ± 0.175 |
| Fengshiping | 24 | 7.10 ± 2.13 | 4.10 ± 1.79 | 0.310 ± 0.177 | 0.137 ± 0.099 |
| Fengshiping | 48 | 6.00 ± 1.83 | 1.70 ± 1.95 | 0.121 ± 0.109 | 0.024 ± 0.026* |
| *Tripterygium hypoglaucum* (Level) Hutch | 8 | 6.11 ± 1.27 | 2.56 ± 1.67 | 0.223 ± 0.122 | 0.074 ± 0.045 |
| Ketotifen | 0.1 | 2.78 ± 1.64** | 0.67 ± 1.41 | 0.033 ± 0.024** | 0.027 ± 0.019* |

Compared to control group *P < 0.05, **P < 0.01

TABLE 3.4

Effect of Fengshiping on AA mouse humoral immune function

| Group | Dose (g/kg) | Medication administration time | PFC (OD) | IgM(Log$_2$) |
|---|---|---|---|---|
| Control group | — | 8 | 0.819 ± 0.013# | 6.875 ± 0.641 |
| AA model control group | — | 10 | 0.940 ± 0.019** | 7.700 ± 0.599* |
| Fengshiping | 5 | 8 | 0.834 ± 0.012**# | 6.875 ± 0.641# |
| Fengshiping | 10 | 8 | 0.834 ± 0.12**# | 6.750 ± 0.886# |
| Fengshiping | 20 | 8 | 0.830 ± 0.014**# | 6.375 ± 0.518## |
| *Tripterygium wilfordii* polyglucoside | 0.012 | 10 | 0.835 ± 0.015**# | 6.950 ± 0.597# |

Compared to the control group
*P < 0.05,
**P < 0.01;
compared to the model group
P < 0.05,
P < 0.01

From Table 3.4 it can be seen that AA mouse PFC and IgM are clearly higher than in normal mice, and Fengshiping is clearly able to reduce AA mouse spleen antibody formation cells (PFC) and antibody (IgM) formation.

Experiment 4. Effect on Rat Passive Cutaneous Anaphylactic (PCA) Reaction.

Rats received a muscular injection of 10 mg/kg egg albumin. at the same time they were immunized by abdominal cavity injection of 0.2 mL $2\times10^{10}$/mL *Bordetella pertussis*. After two weeks the rats were sacrificed and exsanguinated. The serum was segregated to make ready for use.

60 rats weighing 150-200 g, half male and half female, were randomly divided into 6 groups. They were lightly anesthetized under ether at a dorsal site with the fur shaved away and intradermally injected with 0.1 mL of the above-de- It can be seen in Table 4 that Fengshiping's inhibitory effect on rat PCA is weak and it is only at large doses that there is a clear difference compared to the control.

Experiment 5. Effect on Cytokines.

5.1 Effect on Murine TNFα and IL-2

60 ICR mice weighing 18-22 g, half male and half female, were randomly divided into 6 groups, each perfused with different doses of Fengshiping or other medications, once per day for 10 days. 24 h after the final dose of medication, under sterile conditions, mice peritoneal cavity macrophages or spleen cells were taken and Hank's solution was used to wash twice. Washing was performed once using serum-free RPMI 1640 solution, the cell suspension was adjusted to $2\times10^8$/mL using a 5% FCS-RPMI 1640 solution, LPS 10 ng/mL or 10 ng/mL Con A was added, respectively, and culture was carried out for 48 h at 37° C. under 5% $CO_2$. TNFα or IL-2 was detected.

TNFα Determination:

On a murine anti-TNFα monoclonal antibody plate, after restoring to room temperature, 50 μL/well of culture supernatant was added. After 60 min, biotin-labeled antibody was added. After 2 h at 25° C., enzyme-carrying avidin added. After 30 min a stop solution was added. The OD value was detected at 450 nm wavelength. According to the OD value on the standard curve, TNF-α level (ng/mL) was calculated.

IL-2 Determination:

Logarithmic formation phase IL-2 formation-dependent CTLL cells were adjusted using 5% FCS-RPMI 1640 to form a $1\times10^5$/L cell suspension. To the 96-well flat bottom cell culture plate were added a 100 μL/well CTLL cell suspension and 100 μl/well culture supernatant solution. Each sample was repeated in 3 wells, at the same time different dilution strength standard rHIL-2 and culture solution controls were performed. At 37° C. and under 5% $CO_2$ culture was performed for 24 h, followed by centrifugation at 6 h before the culture was interrupted. 110 μL/well supernatant was removed, 10 μL/well of MTT added, and after 3 h at 37° C., OD 570 nm and 630 nm values were detected, for each well OD value=OD 570 nm-OD 630 nm.

$$IL\text{-}2 \text{ activity} = \frac{\text{Sample } \overline{OD} - \text{culture solution control } \overline{OD}}{\text{Standard product } \overline{OD} - \text{culture solution control } \overline{OD}} \times$$

standard product activity unit (IU/mL)

TABLE 5.1

Effect of Fengshiping on TNF and IL-2

| Drug reference | Dose (g/kg) | Number of mice (per group) | TNF (pg/mL) | IL-2 (IU/mL) |
|---|---|---|---|---|
| Control group | — | 10 | 87.80 ± 14.63 | 26.30 ± 4.22 |
|  | 12 | 10 | 62.14 ± 13.13** | 16.00 ± 2.89** |
| Fengshiping | 24 | 10 | 58.60 ± 9.63** | 18.80 ± 2.86** |
|  | 36 | 10 | 54.40 ± 10.88** | 18.20 ± 2.86** |
| Tripterygium wilfordii polyglucoside | 8 | 10 | 58.25 ± 10.32** | 16.00 ± 2.88** |
| Cyclo-phosphamide | 0.02 | 10 | 42.20 ± 9.57** | 10.00 ± 3.00** |

*P < 0.05,
**P < 0.01

The results in Table 5.1 show that Fengshiping has a clear inhibition effect on TNFα. At 12 g/kg it can be seen to have an extremely clear inhibitory effect; the larger the dose the stronger the effect, however the dose-efficacy curve is level. For IL-2, Fengshiping also has a clear inhibitory effect, but the dose-efficacy relationship is unclear.

5.2 Effect on IL-1 and IL-6.

70 NIH mice weighing 18-22 g, half male and half female, were randomly divided into 7 groups, each perfused with different doses of Fengshiping or other medications, once per day for 10 days, and sacrificed 24 h after the final medication was administered. The methodology described below was used to detect IL-1 and IL-6 for abdominal cavity macrophages and spleen cells.

IL-1 Detection:

Under sterile conditions, abdominal cavity macrophages were obtained, washed twice with Hank's solution, washed once with serum-free RPMI 1640, adjusted with 5% FCS-RPMI 1640 to form a $4 \times 10^6$/mL cell suspension; 1 mL was placed in a Kahn tube, cultured for 1 h at 37° C. under 5% $CO_2$, and non-adhered cells removed. 5% FCS-RPMI 1640 and LPS (10 ng/mL) were added, followed by culturing for 72 h at 37° C. under 5% $CO_2$, and repeated freezing and thawing, and then storage at 4° C. Separately, C57 mice were obtained, and thymus gland cells were removed under sterile conditions and adjusted with 5% FCS-RPMI 1640 to form a $1 \times 10^5$/mL cell suspension.

100 μL each of the thymus gland cell suspension and frozen and thawed supernatant was added to a 96-well, flat bottom cell culture plate, three wells for each sample, at the same time different dilutions of standard product rHIL-1 and culture solution served as a control. Then 2 ng/well of ConA was added and the plate was placed at 37° C. under 5% $CO_2$ for 72 h. 14 h before the culture was interrupted, 0.1 μCi/well $^3$H-TdR was added and a multi-head cell collection device to collect the cells and detect the cpm value.

$$IL\text{-}1 \text{ activity} = \frac{\text{Sample } \overline{cpm} - \text{culture solution control } \overline{cpm}}{\text{Standard product } \overline{cpm} - \text{culture solution control } \overline{cpm}} \times$$

standard product activity unit (ng/mL)

IL-6 Detection:

Under sterile conditions, murine spleen cells were obtained, washed twice with Hank's solution, washed with serum-free RPMI 1640 once, and adjusted with 5% FC-RPMI 1640 to form a $2 \times 10^6$/mL cell suspension. 1 mL was placed in a Kahn tube, ConA (10 ng/mL) was added, and culturing was performed for 72 h at 37° C. under 5% $CO_2$ conditions.

Logarithmic formation phase IL-6 dependent formation MH60 cells were adjusted with 5% FC-RPMI 1640 to form a $1 \times 10^5$/mL cell suspension.

100 μl/well of MH60 cell suspension was added to a 96-well, flat bottom cell culture plate, 25 μL/well of culture supernatant, 200 μL/well of 5% FCS-RPMI 1640 were added to make up the deficiency, three wells for each sample. At the same time, different dilutions of standard rHIL-6 and culture solution control were produced. It was cultured at 37° C. under 5% $CO_2$ for 72 h, 6 h before the culture was interrupted it was centrifuged, 110 μL/well of supernatant obtained, MTT 10 μL/well added, at 37° C. for 3 h, OD570 nm and OD630 nm values detected, for each well OD value=OD570 nm-OD630 nm.

$$IL\text{-}2 \text{ activity} = \frac{\text{Sample } \overline{OD} - \text{culture solution control } \overline{OD}}{\text{Standard product } \overline{OD} - \text{culture solution control } \overline{OD}} \times$$

sample dilution × standard product activity unit (IU/mL)

5.2. Effect on murine IL-1 and IL-6.

| Drug reference | Dose (g/kg) | Number of mice (per group) | IL-1 (ng/mL) | IL-6 (IU/mL) |
|---|---|---|---|---|
| Control group | — | 10 | 78.7 ± 7.1 | 94.6 ± 6.8 |
|  | 7.5 | 10 | 59.3 ± 4.9** | 64.9 ± 4.8* |
| Fengshiping | 15 | 10 | 53.3 ± 5.7** | 60.5 ± 4.3** |
|  | 30 | 10 | 54.4 ± 4.8** | 56.0 ± 4.6 |
|  | 60 | 10 | 47.0 ± 16.6* | 56.6 ± 6.1** |
| Tripterygium hypoglaucum (Level) Hutch | 5 | 10 | 57.6 ± 4.7** | 65.7 ± 4.9** |
| Cyclophosphamide | 0.02 | 9 | 44.5 ± 7.7 | 49.6 ± 6.7** |

From the table it can be seen that Fengshiping has a strong inhibitory effect on mice abdominal cavity macrophage formation IL-1 and spleen cell formation IL-6, and as the dose increases the effect increases.

5.3 Effect on Plasma NO in Adjuvant Arthritis in Rats

60 SD rats weighing 160-200 g, half male and half female, were randomly divided into 6 groups; in the blank control group, the right rear foot metatarsal of each rat was intradermally injected with 0.5 mL NS. In the model group and the Fengshiping high, middle and low dose groups and the Tripterygium wilfordii polyglucoside group, the right rear foot metatarsal of each rat was intradermally injected with 0.5 mL Freund's complete adjuvant (FCA). After 18 days the rat adjuvant arthritis model had been created, and gravage administration of medication was started, once per day for five days. The blank control group and the model group were administered distilled water. The high, medium and low dose groups, respectively, were administered high, medium and low doses of Fengshiping, and the positive control group was administered *Tripterygium wilfordii* polyglucoside tablets. One hour after the final dose of medication, 2 mL of blood was taken from the abdominal aorta, the plasma was separated and stored at −70° C. for future testing. NO determination was performed according to the instructions in the NO reagent kit: 0.6 mL reagent C was added to 0.1 mL plasma and mixed thoroughly, 0.4 mL double-distilled water was added, mixed thoroughly, 0.1 mL reagent D added and mixed thoroughly, incubated on ice for 60 min, centrifuged at 12,000 rpm for 2 min, 0.4 mL double-distilled water and 0.1 mL reagent A added to 0.6 mL supernatant; after incubation on ice for 15 min, 0.1 mL reagent B was added, it was placed at room temperature for 1 h, and at 545 nm the specific color OD value was determined. According to the sample's OD value, the standard curve was used to calculate NO levels. The results can be seen in Table 5.3.

TABLE 5.3

Effect of Fengshiping on adjuvant arthritis rat plasma NO

| Drug reference | Dose (g/kg) | Number of mice (per group) | NO level (μmol/L) | y (y-ILgx) |
|---|---|---|---|---|
| Control group | — | 8 | 13.55 ± 1.11* | 1.131 ± 0.032 |
| AA model group | — | 9 | 17.56 ± 4.15** | 1.235 ± 0.097 |
| Fengshiping | 12 | 7 | 9.83 ± 2.58**ΔΔ | 0.985 ± 0.087 |
| Fengshiping | 24 | 7 | 10.12 ± 1.56**ΔΔ | 1.001 ± 0.067 |
| Fengshiping | 48 | 7 | 10.70 ± 1.51**ΔΔ | 1..026 ± 0.062 |
| *Tripterygium wilfordii* polyglucoside | 0.006 | 7 | 15.25 ± 3.48 | 1.173 ± 0.099 |

Compared to the model group
*P < 0.05,
**P < 0.01;
compared to *Tripterygium wilfordii* polyglucoside
ΔΔP < 0.01

From Table 5.3 it can be seen that the rat plasma NO level in the model group is clearly higher than in the blank control group and Fengshiping is clearly able to reduce AA rat plasma NO levels. *Tripterygium wilfordii* polyglucoside tablets are also able to reduce arthritic rat plasma NO levels; however the effect is clearly weak.

Experiment 6. Effect on Murine T Lymphocytes, $CD_4$, $CD_8$ and NK Cells.

6.1. Effect on Normal Murine Lymphocyte Conversion

80 NIH mice, half male and half female, were randomly divided into 8 groups, perfused with different medications, once per day for 10 days. 24 h after the final dose of medication, the mice were sacrificed, and under sterile conditions murine spleen cells were obtained, washed twice with Hank's solution, washed once with serum-free RPMI 1640, and adjusted with 5% FCS-RPMI 1640 to form a $2 \times 10^6$/mL cell suspension. The cell suspension was added to a 96-well flat bottom cell culture plate, 100 g μL/well, 3 wells each part, to which stimulant (ConA 2 ng/well) was added to 2 wells to serve as conversion wells, additionally 1 well had no stimulant added and served as a control well. The plate was placed at 37° C. under 5% $CO_2$ to culture for 72 h. 14 h before the culture was interrupted, 0.1 μCi/well $^3$H-TdR was added. A multi-head cell collection device was used to collect cells, the cpm values were detected and the average value calculated for the multiple wells. Each group's cpm or stimulation index was used directly to perform the comparison. The stimulation index was calculated using the formula below:

$$\text{Stimulation index} = \frac{(\text{Stimulation } \overline{\text{cpm}})}{(\text{Control } \overline{\text{cpm}})}$$

See Table 6.1 for results.

TABLE 6.1

Effect on ConA-induced murine lymphocyte conversion

| Drug reference | Dose (g/kg) | Number of mice (per group) | cpm | Stimulation index |
|---|---|---|---|---|
| Control | — | 10 | 20433 ± 3579 | 25.87 ± 3.06 |
|  | 7.5 | 10 | 13566 ± 1779** | 27.29 ± 7.67 |
|  | 15 | 10 | 12708 ± 1692** | 18.04 ± 3.76 |
| Fengshiping | 30 | 10 | 12809 ± 2575** | 16.17 ± 4.37 |
|  | 60 | 10 | 12090 ± 1706** | 19.05 ± 3.80 |
|  | 2.5 | 10 | 18038 ± 3359 | 17.11 ± 2.60 |
| *Tripterygium hypoglaucum* (Level) Hutch | 5 | 10 | 12081 ± 1039** | 17.58 ± 4.37 |
| Cyclophosphamide | 0.02 | 9 | 9922 ± 1145** | 13.66 ± 2.28 |

Compared to the control
*P < 0.05,
**P < 0.01

From Table 6.1 it can be seen that Fengshiping has a clear inhibitory effect on ConA-induced lymphocyte conversion and shows a definite dose-efficacy relationship.

6.2. Effect on Normal Murine $CD_4$, $CD_8$ and NK Cells.

The same experiment as in 5.1 was conducted. 24 h after medication was terminated, 5% FCS-RPMI 1640 was used to prepare a murine spleen cell suspension, the cell count was adjusted to $2 \times 10^8$/mL and $CD_4$, $CD_8$, and their ratio and NK cells were determined.

Determination of $CD_4$ and $CD_8$:

A 50 μL murine spleen cell suspension was added to polylysine-coated glass slides to prepare a cell smear. Murine T cells were used as the positive control. After the cell smear was fixed with acetone, normal murine serum was used to seal, human biotin-labeled anti-$CD_4$ and $CD_8$ antibodies were added, followed by incubation at 37° C. for 2 h. enzyme-carrying avidin was added, placed at room temperature for 10 min, substrate added for 10 min, washed, and hematoxylin counter-staining was performed for 2 min. After gradient alcohol dehydration, gelatin glycerin was used to seal the slides, and 200 cells were counted under a high-magnification microscope.

$$\text{Cell level} = \frac{\text{Color cell count}}{200} \times 100\%$$

NK Cell Determination:

EC cell preparation: Under sterile conditions, murine spleen cells were obtained, washed with Hank's solution twice, washed once with serum-free RPMI 1640, and adjusted using 5% FCS-RPMI 1640 to form a $2 \times 10^8$/mL cell suspension, to serve as EC.

TC cell preparation: Logarithmic growth phase murine NK cell-sensitive Yack-1 cells were adjusted to form a $4 \times 10^4$/mL cell suspension, to serve as TC.

Determination: 100 μl, each of EC and TC were added to a 96-well flat bottom cell culture plate, 3 duplicate wells per sample, at the same time EC and TC served as controls (EC control: 100 μL EC+100 μL 5% FCS RPMI 1640; TC control: 100 μL TC+100 μL 5% FCS RPMI 1640). At 37° C. and 5% $CO_2$ conditions, culture was performed for 24 h; 6 h before the culture was interrupted it was centrifuged, 110 μL/well supernatant removed, MTT 10 μL/well added, OD570 nm and OD630 nm values detected at 37° C. for 3 h, OD value=OD570 nm-OD630 nm per well.

$$NK\ activity = \left(1 - \frac{Sample\ \overline{OD} - EC\ control\ \overline{OD}}{TC\ control\ \overline{OD}}\right) \times 100\%$$

6.3. Effect on AA Murine Lymphocyte Count and Function.

20±2 g NIH mice were each intradermally injected at the rear right foot metatarsal with 0.05 mL Freund's complete adjuvant, and after three weeks an adjuvant arthritis model was ready. In the negative control group, the rear right foot metatarsal of each mouse was intradermally injected with 0.05 mL physiological saline. Medication was administered via perfusion, once per day for 5 days. After 5 days, peripheral blood slides were prepared for each group of mice to perform esterase staining. Under an oil immersion microscope the esterase stain positive cell percentage (i.e., peripheral blood T cell percentage) was measured. After the mice were anesthetized, the spleen was prepared into a monocyte suspension, washed with PBS once, the supernatant removed, and 4 mL of red cell solution added; after shaking for 2-3 min for complete

TABLE 6.2

Effect of Fengshiping on $CD_4$, $CD_8$ and NK cells

| Group | Dose (g/kg) | Number of mice (per group) | $CD_4$ (%) | $CD_8$ (%) | $CD_4/CD_8$ | NK |
|---|---|---|---|---|---|---|
| Control | — | 10 | 20.80 ± 2.94 | 14.80 ± 2.49 | 1.42 ± 0.18 | 40.13 ± 4.89 |
| Fengshiping | 12 | 10 | 19.14 ± 2.91 | 13.43 ± 2.51 | 1.43 ± 0.08 | 31.94 ± 4.52**ΔΔ |
|  | 24 | 10 | 17.30 ± 2.51** | 12.00 ± 2.40 | 1.46 ± 0.16 | 35.36 ± 3.40*ΔΔ |
|  | 36 | 10 | 16.30 ± 2.50** | 11.23 ± 2.94** | 1.49 ± 0.20 | 31.06 ± 3.53**ΔΔ |
| *Tripterygium hypoglaucum* (Level) Hutch | 8 | 10 | 16.25 ± 2.25** | 11.50 ± 2.45 | 1.44 ± 0.18 | 32.20 ± 2.00** |
| Cyclophosphamide | 0.02 | 10 | 11.50 ± 2.50** | 4.10 ± 1.20** | 2.91 ± 0.53** | 23.10 ± 3.66** |

Compared to the control group *P < 0.05, **P < 0.01; compared to cy ▲▲P < 0.01

From Table 6.2 it can be seen that Fengshiping had a definite inhibitory effect on $CD_4$ and $CD_8$ cells and also presented a dose efficacy relationship, however the dose-efficacy curve was level. For $CD_4$ inhibition, the effective dose was 24 g/kg, and for $CD_8$ cells thus it was only the 36 g/kg high dose that had a clear inhibitory effect. Correspondingly, Fengshiping had no clear effect on the $CD_4/CD_8$ ratio. Cyclophosphamide then had a strong inhibitory effect on $CD_4$ and $CD_8$ and the effect on $CD_8$ was especially strong. These results caused a greater increase in $CD_4/CD_8$ ratio.

Fengshiping also had clear inhibition against NK cells. However, the dose efficacy relationship was not clear. Cyclophosphamide had an intense inhibitory effect, 20 mg/kg was compared to the effect of 12, 24, and 36 g/kg Fengshiping, and for all there was an extremely clear difference.

red cell lysis, it was centrifuged to remove the supernatant, and washed twice with fluorescence wash solution. After it was centrifuged, the supernatant was removed and cell concentration was adjusted to $1 \times 10^6$/mL. To each tube were added 50 μL of diluted anti-$CD_4$ and $CD_8$ antibodies, followed by incubation at 4° C. for 1 h. After it was washed twice with fluorescence wash solution 2 mL of fixing solution was added. A 400-mesh filter was used to filter into a FCA tube and an upflow-style cell instrument was used for analysis. The results can be seen in Table 6.3.

TABLE 6.3

Effect on adjuvant arthritis murine T cells

| Group | Dose (g/kg) | ANAE+ (%) | CD4+ (%) | CD8 (%) | CD4+/CD8+ |
|---|---|---|---|---|---|
| Control group | — | 50.60 ± 4.25 | 26.13 ± 1.16 | 15.56 ± 0.68 | 1.68 ± 0.08 |
| AA Model group | — | 49.00 ± 4.22Δ | 32.56 ± 2.87** | 13.59 ± 1.03** | 2.49 ± 0.16** |
| Fengshiping | 7.5 | 49.13 ± 4.03Δ | 27.30 ± 1.76##Δ | 15.98 ± 1.11##Δ | 1.71 ± 0.04##Δ |
|  | 15 | 49.31 ± 3.29Δ | 27.96 ± 1.67##Δ | 16.23 ± 1.27##Δ | 1.73 ± 0.05##Δ |
|  | 30 | 48.56 ± 3.23Δ | 26.75 ± 1.94##Δ | 15.58 ± 1.29##Δ | 1.72 ± 0.04##Δ |
| *Tripterygium wilfordii* polyglucoside | 0.012 | 48.88 ± 2.89Δ | 27.88 ± 1.99##Δ | 16.33 ± 1.31##Δ | 1.70 ± 0.03##Δ | n = 8, compared to the control group *P < 0.05, **P < 0.01. compared to the model group #P < 0.05, ##P < 0.01. compared to the control group ▲P < 0.05

From Table 6.3 it can be seen that in ANAE positive cells, the various groups showed no clear difference, however AA murine $CD_4$ cells were clearly increased, and $CD_s$ cells were clearly reduced, thus $CD_4/CD_8$ was clearly elevated, and Fengshiping therapy is able to restore abnormal $CD_4$, $CD_8$, and $CD_4/CD_8$ antibodies to normal levels.

Experiment 7. Effect on Murine Abdominal Cavity Macrophage Phagocytic Function

50 NIH mice, weighing 18-22 g, half male and half female, were randomly divided into 5 groups, each perfused with the same volume at different doses of medication solution, once per day for one week. 1 h after the final dose of medication, the abdominal cavity of each mouse was infused with 0.2 mL 10% chicken red blood cells, after 4 h the mice were sacrificed, and abdominal cavity fluid obtained. The drip slide method was used to observe microscopically and determine the phagocytic CRBC macrophage count. The figures for macrophage phagocytic CRBC are shown in Table 7.

TABLE 7

Effect of Fengshiping on ICR murine abdominal cavity macrophage CRBC capacity

| Group | Dose (g/kg) | Number of mice (per group) | Phagocytic percentage | Phagocytic index |
|---|---|---|---|---|
| Control | — | 10 | 25.75 ± 9.40 | 1.28 ± 0.20 |
| Fengshiping | 27 | 10 | 33.20 ± 12.77 | 1.46 ± 0.36 |
| Fengshiping | 40.5 | 10 | 35.20 ± 10.16 | 1.21 ± 0.20 |
| Fengshiping | 60.9 | 10 | 37.78 ± 20.14 | 1.53 ± 0.32 |
| Dexamethasone | 0.005 | 10 | 8.33 ± 10.13* | 1.10 ± 0.18 |

*P < 0.05

From Table 7 it can be seen that at doses 27, 40.5 and 60.9 g/kg, Fengshiping had no clear effect on murine abdominal cavity macrophage phagocytic function.

Experiment 8. Effect on Murine Abdominal Cavity Capillary Vessel Hyperpermeability.

90 NIH mice, weighing 18-22 g, half male and half female, were randomly divided into 9 groups, respectively, and perfusion was performed with the same volume at differing doses of medication solution one time or once per day for 3 days. 1 h after the final medication dose, 0.7% HAC physiological saline solution was injected into the abdominal cavity of each mouse, and at the same time an iv of 0.1 mL/10 g 0.5% Evans blue physiological saline solution was administered. After 30 min the mice were sacrificed cervical vertebrae disjoint, the abdominal cavity was cut open, 5 mL physiological saline was used incrementally to rinse the abdominal cavity of each mouse, the rinsing solution was aspirated out, combined, and physiological saline was added at a constant volume to 8 mL/mouse. After centrifuging at 3000 rpm, the supernatant was used at a wavelength of 590 nm to detect the OD value. The results are shown in Table 8.

TABLE 8

Effect of Fengshiping on acetic acid-induced murine abdominal cavity capillary vessel hyperpermeability

| Group | Dose (g/kg) | Medication administration frequency | Number of mice (per group) | Dye permeability | P value |
|---|---|---|---|---|---|
| Control | — | — | 10 | 0.29 ± 0.13 | |
| Fengshiping | 27 | qd*1 | 10 | 0.26 ± 0.14 | >0.05 |
| Fengshiping | 40 | qd*1 | 10 | 0.25 ± 0.10 | >0.05 |
| Fengshiping | 60 | qd*1 | 10 | 0.25 ± 0.09 | >0.05 |
| Control | — | — | 10 | 0.28 ± 0.15 | |
| Fengshiping | 27 | qd*3 | 10 | 0.25 ± 0.12 | >0.05 |
| Fengshiping | 40 | qd*3 | 10 | 0.18 ± 0.10 | >0.05 |
| Fengshiping | 60 | qd*3 | 10 | 0.15 ± 0.13 | >0.05 |
| Dexamethasone | 0.15 | qd*3 | 10 | 0.11 ± 0.07 | >0.01 |

From Table 8, the effect of Fengshiping on acetic acid-induced murine abdominal cavity capillary vessel hyperpermeability can be seen. When medication was administered once there was no clear effect, but when medication was administered three days in succession there were clear inhibition results.

Experiment 9. Effect of Carrageenan-Induced Murine Pleuritis Exudation and Inflammatory Cell Aggregation After the mice were randomly divided into groups, at the tail vein each mouse was infused at 0.1 mL/10 g body weight with 0.5% Evans blue physiological saline solution. The mice were lightly anesthetized with ether and at 0.03 mL/animal the right thoracic cavity was infused using a specially prepared syringe with a 1% carrageenan solution. At 4 h and 32 h after inflammation was induced, the mice were sacrificed, the abdomen was cut open to expose the diaphragmatic muscle, 1 mL injection device was used twice to infuse a total of 2 mL thoracic cavity washing solution, and the washing solution was collected in a test tube. 20 μL of the above-described washed out solution was added to 400 μL of white blood cell dilution solution, and a white blood cell blood count was performed under a microscope. The remaining solution was centrifuged at 3000 rpm for 10 min, supernatant was taken and at a wavelength of 600 nm site the optical density was detected. The thoracic cavity washing solution was used to correct the original solution to zero. The results can be seen in Table 9.

TABLE 9

Effect of Fengshiping on deerhorn vegetable capsule-induced murine pleuritis cell aggregation

| Group | Dose (g/kg) | White blood cell count ($2 \times 10^5$) | | Dye exudation (OD) | |
|---|---|---|---|---|---|
| | | 4 h | 32 h | 4 h | 32 h |
| Control | — | 46.0 ± 6.9 | 16.0 ± 9.6 | 0.156 ± 0.066 | 0.109 ± 0.019 |
| Fengshiping | 27 | 26.8 ± 4.5* | 14.2 ± 8.0 | 0.121 ± 0.062 | 0.116 ± 0.031 |
| Fengshiping | 40.5 | 10.9 ± 4.0** | 17.3 ± 4.6 | 0.100 ± 0.048 | 0.153 ± 0.032 |
| Fengshiping | 60 | 8.0 ± 5.5*** | 6.6 ± 4.7* | 0.129 ± 0.066 | 0.092 ± 0.051 |
| Control | 0.05 | 12.7 ± 10.2** | 4.4 ± 4.0* | 0.085 ± 0.045 | 0.063 ± 0.017 |

From Table 9 it can be seen that Fengshiping had clear inhibition results against murine pleuritis white blood cell aggregation. This effect was especially strong at early-stage aggregation; at 4 h the regression equation y=44.13−2.01x, r=−0.9625 was obtained, weak against late-stage aggregation, and at 20 g/kg dose there were clear results and the effect on pleuritis exudation was not clear.

Experiment 10. Effect on Rat CMC Sac Autologous Cell Aggregation.

64 SD rats weighing 150-180 g, half male and half female, were randomly divided into 8 groups, respectively, perfused with identical volume different doses of medication solution, one time or once per day for three days. One day prior to the day of the experiment, a 20 mL air sac was created at the back of the rat, into which was injected 20 mL of a 1% CMC solution. At 3.5 h and 7.5 h, 0.1 mL was aspirated out of each animal, placed in 0.01% brilliant cresyl blue PBS solution for staining, and under a microscope the CMC sac fluid white blood cell count was taken. The results are shown in Table 10.

TABLE 10

Effect of Fengshiping on rat carboxymethylcellulose sac white blood cell count

| Group | Dose (g/kg) | Rat count (per group) | WBC count ($\times 10^7$/L) 3.5 h | 7.5 h |
|---|---|---|---|---|
| Control | — | 8 | 9.7 ± 1.2 | 57.7 ± 17.3 |
| Fengshiping | 27 ×1 | 8 | 8.5 ± 3.5 | 39.4 ± 16.5 |
| Fengshiping | 40 ×1 | 8 | 8.7 ± 7.3 | 35.3 ± 23.2 |
| Fengshiping | 60 ×1 | 8 | 6.6 ± 3.3 | 18.1 ± 8.6** |
| Control | — | 8 | 10.97 ± 6.7 | 35.6 ± 11.2 |
| Fengshiping | 27 × 3 | 8 | 15.4 ± 9.7 | 38.6 ± 15.5 |
| Fengshiping | 40 × 3 | 8 | 4.8 ± 3.4** | 18.4 ± 12.2** |
| Fengshiping | 60 × 3 | 8 | 3.0 ± 2.8** | 11.0 ± 9.2* |
| Prednisone | 0.1 × 3 | 8 | 14.2 ± 8.0 | 41.7 ± 16.0 |
| Control | — | 8 | 10.9 ± 3.0 | 41.3 ± 6.9 |
| Fengshiping | 18 ×7 | 8 | 6.2 ± 3.0* | 11.4 ± 6.4* |
| Fengshiping | 27 ×7 | 8 | 3.7 ± 1.7** | 6.4 ± 3.1** |
| Fengshiping | 40 ×7 | 8 | 2.5 ± 1.9** | 5.9 ± 3.9** |
| Prednisone | 2 mg ×1 | 8 | 1.5 ± 0.7** | 3.0 ± 1.0** |

Compared to the control
**P < 0.01

From Table 10 it can be seen that Fengshiping had a clear inhibitory effect on white blood cell aggregation in rat CMC sac and showed a clear dose-efficacy relationship. As medication administration time was extended the effect intensified; medication was administered for 7 days, at and 18 g/kg, e.g., it had an extremely clear inhibitory effect on white blood cell migration and prednisone intracapsular injection also had strong inhibition results.

Experiment 11. Effect on Croton Oil-Induced Murine Ear Inflammation

60 NIH mice, weighing 18-22 g, half male half female, were randomly divided into 6 groups, each perfused with the same volume in different doses of medication solution or *Astragalus* solution, once per day for three days. 1 h after the final medication administration, the left ear of each mouse was uniformly smeared on both sides of the auricle with 0.02 mL of 2% croton oil compound. After 4 h each mouse was sacrificed by cervical vertebrae disjoint, the left and the right ears cut out and the inflamed ear and the control ear weighed. The difference in weight in mg between the right and left ear was used to express the degree of ear inflammation. The results can be seen in Table 11.

TABLE 11

Effect of Fengshiping on croton oil-induced murine ear inflammation

| Group | Dose (g/kg) | Number of mice (per group) | Degree of ear inflammation (mg) | Inhibition rate | P value |
|---|---|---|---|---|---|
| Control | — | 10 | 44.38 ± 9.40 | | |
| Fengshiping | 27 | 10 | 39.05 ± 12.33 | 12.00 | >0.05 |
| Fengshiping | 40 | 10 | 36.65 ± 5.83 | 17.64 | <0.05 |
| Fengshiping | 60 | 10 | 34.91 ± 9.71 | 21.34 | <0.05 |
| Dexamethasone | 0.003 | 10 | 14.13 ± 5.75 | 68.16 | <0.01 |

From Table 11 it can be seen that Fengshiping had a clear inhibitory effect on croton oil-induced ear inflammation in mice, and it had a dose-efficacy relationship. However, the dose-efficacy relationship curve was fairly level, and at 13.5 g/kg there were clear inhibition results.

Experiment 12. Effect on Acetic Acid-Induced Body-Twisting Reaction in Mice.

60 Kunming mice, weighing 18-22 g, half male half female, were randomly divided into 6 groups, each perfused with different doses of medication solution or *Astragalus* solution. 1 h after medication administration, 0.2 mL 0.7% HAC physiological saline solution was injected into the abdominal cavity. The mice were placed in fiberglass to observe the various latent stage body-twisting reactions for each mouse and body-twisting frequency in a 20-min period. The results are shown in Table 12.

TABLE 12

Effect of Fengshiping on acetic acid-induced murine body-twisting frequency

| Group | Dose (g/kg) | Number of mice (per group) | Body-twisting frequency | Latent period (min) |
|---|---|---|---|---|
| Control | — | 10 | 34.6 ± 14.1 | 3.13 ± 0.80 |
| Fengshiping | 27 | 10 | 28.2 ± 5.76 | 3.82 ± 0.85 |
| Fengshiping | 40 | 10 | 31.0 ± 18.4 | 3.86 ± 2.00 |
| Fengshiping | 60 | 10 | 20.7 ± 12.3* | 3.95 ± 1.42 |
| *Tripterygium hypoglaucum* (Level) Hutch | 20 | 10 | 25.1 ± 11.9 | 3.60 ± 0.93 |
| Morphine hydrochloride | 10 mg/kg | 10 | 0.0 ± 0.0 | 0.00 ± 0.00 |

From Table 12 it can be seen that at a greater dose, Fengshiping was able to delay the onset of acetic acid-induced body-twisting reaction in mice and to clearly reduce the body-twisting frequency in a 20-min period, showing that Fengshiping had a definite analgesic effect.

Experiment 13. Effect on AA Rat Blood Rheology.

SD rats weighing 180±20 g were each intradermally injected at the right rear foot metatarsal with 0.05 mL Freund's complete adjuvant to prepare an adjuvant arthritis model. In the negative control group, each right rear foot metatarsal was intradermally injected with 0.05 mL physiological saline. Three weeks later the model was ready. The rats were divided into the model group, the high, middle and low dose groups, the negative control group and the positive control group. The positive control group was given *Tripterygium wilfordii* polyglucoside tablets. Medication was administered by perfusion once per day for 5 days. 1 h after the final medication administration, 3 mL of blood was taken from the abdominal aorta, and placed in a 1% heparin anticoagulant test tube. A NXE-1 model cone-style viscometer was used at 230, 115, 46, 23, 11.5 and 5.75 S$^{-1}$ shearing rates to detect whole-blood viscosity. Using the WTP-B II model, it was possible to adjust the constant-pressure capillary vessel viscometer to determine the plasma viscosity. The hematocrit tube centrifuge method was used to detect hematocrit, and the hemagglutination index and the red cell rigidity index were obtained by calculating the above-described results. The results are shown in Table 13.

TABLE 13

Effect on adjuvant arthritis rat blood rheology

| Group | Control group | Model group | Fengshiping (30 g/kg) | Fengshiping (15 g/kg) | Fengshiping (7.5 g/kg) | Tripterygium wilfordii polyglucoside (6 mg/kg) |
|---|---|---|---|---|---|---|
| Whole blood viscosity (mPa · s) | | | | | | |
| $230S^{-1}$ | 4.43 ± 0.09 | 4.92 ± 0.15** | 4.56 ± 0.09## | 4.49 ± 0.11## | 4.54 ± 0.16## | 4.66 ± 0.28# |
| $115S^{-1}$ | 5.17 ± 0.25 | 5.81 ± 0.19 | 5.33 ± 0.09## | 5.32 ± 0.10## | 5.16 ± 0.14## | 5.60 ± 0.48# |
| $46S^{-1}$ | 6.84 ± 0.11 | 7.20 ± 0.18** | 6.56 ± 0.13## | 6.59 ± 0.09## | 6.67 ± 0.14## | 6.70 ± 0.48 |
| $23S^{-1}$ | 8.10 ± 0.15 | 8.23 ± 0.38 | 7.95 ± 0.22 | 7.93 ± 0.12 | 7.97 ± 0.14 | 8.02 ± 0.14 |
| $11.5S^{-1}$ | 9.35 ± 0.08 | 9.78 ± 0.10** | 9.40 ± 0.08## | 9.45 ± 0.10## | 9.30 ± 0.133 | 9.31 ± 0.12## |
| $6.5S^{-1}$ | 11.03 ± 0.14 | 12.66 ± 0.31** | 11.21 ± 0.21## | 11.29 ± 0.19## | 11.60 ± 0.40## | 11.42 ± 0.52# |
| Plasma viscosity (mPa · s) | 1.158 ± 0.032 | 1.248 ± 0.040** | 1.161 ± 0.011## | 1.154 ± 0.023## | 1.156 ± 0.018## | 1.158 ± 0.029# |
| Hematocrit (%) | 46.13 ± 2.31 | 41.33 ± 1.12** | 45.10 ± 2.39## | 44.33 ± 1.52## | 45.71 ± 1.04## | 46.03 ± 3.59# |
| Hemagglutination index | 2.49 ± 0.032 | 2.58 ± 0.083* | 2.46 ± 0.066# | 2.49 ± 0.094# | 2.44 ± 0.048## | 2.45 ± 0.091# |
| Red cell rigidity index | 6.155 ± 0.536 | 7.127 ± 0.557** | 6.506 ± 0.558 | 6.525 ± 0.146 | 6.394 ± 0.200# | 6.621 ± 0.883 |

Compared to the negative control group *P < 0.05, **P < 0.01. compared to the model group #P < 0.05, ##P < 0.01

From Table 13 it can be seen that with the AA rat blood rheology model clear changes appeared, whole blood and blood plasma viscosity increased, hematocrit fell, and the hemagglutination index and rigidity index rose. Fengshiping therapy was able to make the above-described clear improvements to blood rheology indexes.

The above experiments prove the pharmacological effect of Fengshiping. Its many important pharmacological effects all have a good dose-efficacy relationship, showing that clinically it was possible to use a modulating dose to achieve optimal therapeutic efficacy.

Studies of the clinical efficacy of Fengshiping have been conducted in China, Japan, and Australia. With the use of Fengshiping capsules alone, results have been observed showing that, in accordance with international diagnosis, treatment and therapeutic efficacy standards for related disease, Fengshiping is 94% [of the time] somewhat effective against RA, about 60% [of the time] clearly effective, and able to quickly improve morning stiffness, inflammation pain, other symptoms, and RA-related detection indexes, as shown in Tables 14-21.

TABLE 14

Comparison of treatment group and control group results

| Group | Number of cases | Alleviated (clinically cured) | Clear effect | Some effect | No effect | Clear effect rate | Some effect rate |
|---|---|---|---|---|---|---|---|
| Treatment group | 32 | 5 | 14 | 11 | 2 | 59.38 | 93.74 |
| Control group | 30 | 3 | 10 | 12 | 5 | 43.33 | 83.33 |

TABLE 15

Effect on IgG, IgA and IgM

| Group | Number of cases | IgG Before | IgG After | IgA Before | IgA After | IgM Before | IgM After |
|---|---|---|---|---|---|---|---|
| Normal people | 32 | 12.45 ± 1.48 | | 2.37 ± 1.00 | | 1.58 ± 0.59 | |
| Treatment group | 32 | 16.92 ± 3.49 | 14.17 ± 1.39** | 3.65 ± 1.03 | 2.39 ± 1.18** | 1.89 ± 0.88 | 1.48 ± 1.01 |
| Control group | 30 | 17.03 ± 4.12 | 15.14 ± 2.21** | 3.45 ± 1.86 | 2.32 ± 1.75** | 2.03 ± 0.95 | 1.76 ± 1.28 |

Compared to the pre-treatment group **P < 0.01

TABLE 16

Effect on C3 and C4

| Group | Number of cases (per group) | C3 Before | C3 After | C4 Before | C4 After |
|---|---|---|---|---|---|
| Normal people | 32 | 0.62 ± 0.13 | | 0.14 ± 0.15 | |
| Treatment group | 32 | 1.88 ± 0.72 | 1.25 ± 0.66** | 0.48 ± 0.12 | 0.26 ± 0.06* |
| Control group | 30 | 2.13 ± 0.64 | 1.56 ± 0.62** | 0.40 ± 0.16 | 0.25 ± 0.07** |

Compared to the pre-treatment group *$P < 0.05$, **$P < 0.01$

TABLE 17

Effect on ESR and CRP

| Group | Number of cases (per group) | ESR Before | ESR After | CRP Before | CRP After |
|---|---|---|---|---|---|
| Normal people | 32 | 8.37 ± 5.26 | | 4.12 ± 1.88 | |
| Treatment group | 32 | 66.58 ± 30.31 | 30.31 ± 6.53** | 13.35 ± 6.67 | 8.86 ± 3.34* |
| Control group | 30 | 73.33 ± 9.00 | 35.83 ± 11.61** | 14.21 ± 6.29 | 9.04 ± 3.15** |

Compared to the pre-treatment group *$P < 0.05$, **$P < 0.01$

TABLE 18

Comparison of grip strength before and after treatment

| Group | Treatment group Before | Treatment group After | Control group Before | Control group After |
|---|---|---|---|---|
| Grip strength left (mmHg) | 39.13 ± 20.24(15) | 80.47 ± 34.61**(15) | 24.00 ± 17.63(21) | 55.15 ± 23.27**(21) |
| Right | 35.85 ± 22.46(15) | 85.32 ± 36.32**(15) | 22.80 ± 12.32(21) | 58.17 ± 20.59**(21) |

Compared to the pre-treatment group *$P < 0.05$, **$P < 0.01$

TABLE 19

Effect on joint inflammation and pain and morning stiffness

| Item | Treatment group Before | Treatment group After | Control group Before | Control group After |
|---|---|---|---|---|
| Joint inflammation and pain | 5.79 ± 0.52 | 3.14 ± 0.83* | 5.56 ± 2.15 | 2.92 ± 0.26* |
| Morning stiffness time (min) | 50.33 ± 6.47 | 20.24 ± 8.27** | 48.75 ± 8.34 | 27.50 ± 3.78** |

Compared to the pre-treatment group
*$P < 0.05$,
**$P < 0.01$

TABLE 20

Effect on RF negative conversion

| Group | Number of cases | RF negative Before treatment | RF negative After treatment | Negative conversion rate |
|---|---|---|---|---|
| Treatment group | 32 | 24 | 11 | 54.2 |
| Control group | 30 | 18 | 10 | 44.4 |

At the same time that it is able to achieve clear therapeutic efficacy, Fengshiping is also able to reduce the patient's serum SIL-2R, STNF, SIL-6R and other indexes, as shown in Table 21.

TABLE 21

Effect on SIL-2R, STNF, SIL-6R and other primary indexes

| Group | Number of cases | SIL-2R(u/mL) Before | SIL-2R(u/mL) After | STNF R1 (ng/mL) Before | STNF R1 (ng/mL) After | SIL-6R (ng/mL) Before | SIL-6R (ng/mL) After |
|---|---|---|---|---|---|---|---|
| Normal people | 32 | 299 ± 68 (n = 32) | | 1.56 ± 0.48 | | 72.05 ± 18.26 (n = 22) | |
| Fengshiping | 15 | 683 ± 189 | 381 ± 157** | 2.87 ± 0.66 | 1.75 ± 0.54** | 136.18 ± 28.57 | 90.15 ± 20.12** |
| Control group | 10 | 765 ± 203 | 412 ± 167** | 2.63 ± 0.72 | 2.38 ± 0.39 (n = 8) | 148.21 ± 30.31 | 99.02 ± 26.70** |

Compared to pre-treatment **$P < 0.01$

Experience proves that the embodiments described below are able to achieve the above-described invention results.

Embodiment 1

2222 g *Epimedium brevicornum* Maximowicz
2222 g *Tripterygium hypoglaucum* (Level) Hutch
1111 g *Cuscuta chinensis* Lamarck
1111 g *Lycium barbarum* L.

Using the four ingredients above, *Tripterygium hypoglaucum* (Level) Hutch is cut into pieces and 13×, 10× and 10× water is added, followed by three extractions. 1 h each time, *Epimedium brevicornum* Maximowicz is cut into sections, 15×, 10× and 10× the amount of water is added and three extractions are carried out 1 h each time. *Lycium barbarum* L. is pulverized to form a crude material, immersed in 20× water at 80° C. for 1 h. *Cuscuta chinensis* Lamarck is pulverized into a crude powder and immersed in 31× water at 80° C. for 1 h. The water decoctions or the water immersion fluids of the four materials are filtered separately, and separately passed through a large-pore adsorption resin column, then 70% ethanol is used for elution. When the runoff liquid is clearly darker in color, collection of the eluent is started. When the eluent color becomes extremely light, the elution is complete. Ethanol is recovered from each material eluent, concentrated, dried, thus obtaining the final extracted material powder. To each of the four extracted material powders is added medication-use starch to 200 g, mixed thoroughly, and packaged into 1000 capsules. The methods of the present invention are used to prepare a capsule with 0.2 g material inside it, and each capsule contains no less than 2.0 mg *Epimedium brevicornum* Maximowicz $C_{33}H_{40}O_{15}$. Routine indications are: oral, 3 times per day, 3 capsules each time.

Embodiment 2

2000 g *Tripterygium hypoglaucum* (Level) Hutch
2000 g *Epimedium brevicornum* Maximowicz Using the two ingredients above, *Tripterygium hypoglaucum* (Level) Hutch is cut into pieces and 13×, 10× and 10× is water added, followed by three extractions, 1 h each time. *Epimedium brevicornum* Maximowicz is cut into sections and 15×, 10× and 10× is water added, followed by three extractions, 1 h each time. The water decoctions of the materials are filtered and passed through a large-pore adsorption resin column, then 70% ethanol is used for elution. When the color of the runoff liquid is clearly darker, collection of the eluent is started. When the eluent color becomes extremely light the elution is complete. Ethanol is recovered from each material eluent, concentrated and dried, thus obtaining the extracted material powder. The extracted material powder is added to medication-use starch, mixed thoroughly, and packaged into 1000 capsules. The methods of the present invention are used to prepare a capsule packaged with 0.2 g of materials in each capsule, and each capsule contains no less than 2.0 mg *Epimedium brevicornum* Maximowicz $C_{33}H_{40}O_{15}$. Routine indications are: oral, 3 times per day, 3 capsules each time.

Embodiment 3

2000 g *Tripterygium hypoglaucum* (Level) Hutch
2000 g *Epimedium brevicornum* Maximowicz
1000 g *Lycium barbarum* L.

*Tripterygium hypoglaucum* (Level) Hutch is cut into pieces and 13×, 10× and 10× water is added followed by three extractions, 1 h each time. *Epimedium brevicornum* Maximowicz is cut into sections, 15×, 10× and 10× waster is added, followed by three extractions, 1 h each time. *Lycium barbarum* L. is pulverized to form a crude material and immersed in 20× water at 80° C. for 1 h. The water decoctions or the water immersion fluids of the materials are each filtered and passed through a large-pore adsorption resin column, then 70% ethanol is used for elution. When the color of the runoff liquid is clearly darker, collection of the eluent is started. When the eluent color becomes extremely light the elution is complete. Ethanol is recovered from each material eluent, concentrated and dried, thus obtaining an extracted material powder. The extracted material powders are added to medication-use starch, mixed thoroughly, and packaged into 1000 capsules. The methods of the present invention are used to prepare a capsule which is packaged with 0.2 g materials, and each capsule contains no less than 2.0 mg of *Epimedium brevicornum* Maximowicz $C_{33}H_{40}O_{15}$. The routine indications are: orally, 3 times per day, 3 capsules each time.

Embodiment 4

2000 g *Tripterygium hypoglaucum* (Level) Hutch
2000 g *Epimedium brevicornum* Maximowicz
1000 g *Cuscuta chinensis* Lamarck

*Tripterygium hypoglaucum* (Level) Hutch is cut into pieces and 13×, 10× and 10× waster is added, followed by three extractions, 1 h each time. *Epimedium brevicornum* Maximowicz is cut into sections, 15×, 10× and 10× waster is added, followed by three extractions, 1 h each time. *Cuscuta chinensis* Lamarck is pulverized into a crude powder and immersed in 31× water at 80° C. for 1 h. The water decoctions or water immersion fluids of the materials each filtered and passed through a large-pore adsorption resin column, then 70% ethanol is used for elution. When the color of the runoff liquid is clearly darker, collection of the eluent is started. When the eluent color becomes extremely light the elution is complete. Ethanol is recovered from each material eluent, concentrated and dried, thus obtaining the extracted material powder. The extracted material powders are added to medication-use starch, mixed thoroughly, and packaged into 1000 capsules. The methods of the present invention are used to prepare a capsule packaged with 0.2 g materials inside, and each capsule contains no less than 2.0 mg of *Epimedium brevicornum* Maximowicz $C_{33}H_{40}O_{15}$. Routine indications are: orally, 3 times per day, 3 capsules each time.

Embodiment 5

2000 g *Tripterygium hypoglaucum* (Level) Hutch
1000 g *Cuscuta chinensis* Lamarck

*Tripterygium hypoglaucum* (Level) Hutch is cut into slices and 13×, 10× and 10× waster is added, followed by three extractions, 1 h each time. *Cuscuta chinensis* Lamarck is pulverized into a crude powder and immersed in 31× water at 80° C. for 1 h. The water decoctions or water immersion fluids of the materials filtered and passed through a large-pore adsorption resin column, then 70% ethanol is used for elution. When the color of the runoff liquid is clearly darker, collection of the eluent is started. When the eluent color becomes extremely light the elution is complete. Ethanol is recovered from each material eluent, concentrated and dried, thus obtaining the extracted material powder. The extracted material is added to medication-use starch, mixed thoroughly, and packaged into 1000 capsules. The methods of the present invention are used to prepare a capsule with a daily dose equal to 30 g/day.

Embodiment 6

2000 g *Tripterygium hypoglaucum* (Level) Hutch
1000 g *Lycium barbarum* L.

*Tripterygium hypoglaucum* (Level) Hutch is cut into pieces and 13×, 10× and 10× waster is added, followed by three extractions, 1 h each time. *Lycium barbarum* L. is pulverized into a crude material and immersed in 20× water at 80° C. for 1 h. The water decoctions or water immersion fluids of the materials each filtered and passed through a large-pore adsorption resin column, then 70% ethanol is used for elution. When the color of the runoff liquid is clearly darker, collection of the eluent is started. When the eluent color becomes extremely light the elution is complete. Ethanol is recovered from each material eluent, concentrated, and dried, thus obtaining the extracted material powder. The extracted material powder is added to medication-use starch, mixed thoroughly, and packaged into 1000 capsules. The methods of the present invention are used to prepare a capsule with a daily dose equivalent to 30 g/day.

What is claimed is:

1. A pharmaceutical mixture for treating rheumatism, consisting of an alcoholic extract of:
   1-4 parts by weight *Tripterygium hypoglaucum* (Levl.) Hutch.;
   1-4 parts by weight *Epimedium brevicornum* Maxim.;
   1-4 parts by weight *Lycium barbarum* L.; and
   1-4 parts by weight *Cuscuta chinensis* Lam., or *Cuscuta australis* R. Br.

2. The pharmaceutical mixture according to claim 1, wherein
   *Tripterygium hypoglaucum* (Levl.) Hutch. is present in an amount of 2 parts by weight;
   *Epimedium brevicornum* Maxim. is present in an amount of 2 parts by weight;
   *Lycium barbarum* L. is present in an amount of 1 part by weight; and,
   *Cuscuta chinensis* Lam., or *Cuscuta australis* R. Br. is present in an amount of 1 part by weight.

3. A pharmaceutical dosage form of a hard capsule, soft capsule, tablet, granule, or injectable liquid for treating rheumatism, wherein said dosage form contains a pharmaceutical mixture consisting of an alcoholic extract of: *Tripterygium hypoglaucum* (Levl.) Hutch., 1-4 parts by weight of the mixture; *Epimedium brevicornum* Maxim., 1-4 parts by weight of the mixture; *Lycium barbarum* L, 1-4 parts by weight of the mixture; and *Cuscuta chinensis* Lam. or *Cuscuta australis* R. Br., 1-4 parts by weight of the mixture.

* * * * *